(12) United States Patent
Angelsen et al.

(10) Patent No.: US 8,182,428 B2
(45) Date of Patent: *May 22, 2012

(54) DUAL FREQUENCY BAND ULTRASOUND TRANSDUCER ARRAYS

(75) Inventors: Bjørn A. J. Angelsen, Trondheim (NO);
Tonni F. Johansen, Trondheim (NO);
Rune Hansen, Trondheim (NO); Sven Peter Nasholm, Växjö (SE); Svein-Erik Måsøy, Trondheim (NO)

(73) Assignee: SURF Technology AS, Trondheim (NO)

( * ) Notice: Subject to any disclaimer, the term of this patent is extended or adjusted under 35 U.S.C. 154(b) by 592 days.

This patent is subject to a terminal disclaimer.

(21) Appl. No.: 12/351,702

(22) Filed: Jan. 9, 2009

(65) Prior Publication Data

US 2009/0182237 A1    Jul. 16, 2009

Related U.S. Application Data

(60) Provisional application No. 61/010,545, filed on Jan. 9, 2008, provisional application No. 61/011,006, filed on Jan. 14, 2008.

(51) Int. Cl.
*A61B 8/00* (2006.01)
*H01L 41/00* (2006.01)
*H04R 19/00* (2006.01)

(52) U.S. Cl. .................. 600/459; 310/311; 310/327

(58) Field of Classification Search ............ None
See application file for complete search history.

(56) References Cited

U.S. PATENT DOCUMENTS

| 5,410,516 | A | 4/1995 | Uhlendorf et al. | |
|---|---|---|---|---|
| 5,471,988 | A * | 12/1995 | Fujio et al. | 600/439 |
| 6,312,383 | B1 | 11/2001 | Lizzi et al. | |
| 6,461,303 | B2 | 10/2002 | Angelsen | |
| 6,598,601 | B2 | 7/2003 | Schütz | |
| 6,673,016 | B1 * | 1/2004 | Bolorforosh et al. | 600/437 |
| 2002/0042572 | A1 * | 4/2002 | Fukukita | 600/443 |
| 2003/0155290 | A1 | 8/2003 | Chanaud | |
| 2004/0012307 | A1 | 1/2004 | Fukuda et al. | |
| 2004/0267130 | A1 | 12/2004 | Angelsen et al. | |
| 2005/0203397 | A1 * | 9/2005 | Degertekin | 600/437 |

(Continued)

FOREIGN PATENT DOCUMENTS

JP    2251754    10/1990

(Continued)

OTHER PUBLICATIONS

Br Heart 1984 51: Doppler echocardiography in the study of patients with mitral disc valve prostheses pp. 61-69.
2004 IEEE Ultrasonics Symposium: Prototype Dual Frequency Bilaminar Array Transducer Capable of Therapeutic Exposure at 500 kHz and Doppler Monitoring at 2MHz pp. 141-144.
2003 IEEE Ultrasonics Symposium: Dual Frequency Array Transducer for Ultrasonid-Enhanced Transcranial Thrombolysis pp. 680-683.

(Continued)

*Primary Examiner* — Long V Le
*Assistant Examiner* — Lawrence Laryea
(74) *Attorney, Agent, or Firm* — Cozen O'Connor

(57) ABSTRACT

An acoustic probe transmits/receives acoustic pulses with frequencies both in a high frequency (HF), and a selectable amount of lower frequency (LF1, LF2, . . . , LFn, . . . ) bands. The radiation surfaces of at least two of the multiple frequency bands have a common region. The arrays and elements can be of a general type such as annular arrays, phased or switched arrays, linear arrays with division in both azimuth and elevation direction, like a 1.5D, a 1.75D and a full 2D array, or curved arrays. The element division, array type, and array aperture sizes for the different bands can also be different.

51 Claims, 24 Drawing Sheets

U.S. PATENT DOCUMENTS

2005/0240127 A1 * 10/2005 Seip et al. .................. 601/2

FOREIGN PATENT DOCUMENTS

| JP | 4273699 | 9/1992 |
|---|---|---|
| JP | 5277102 | 10/1993 |
| JP | 2002/336248 | 11/2002 |
| JP | 2005103193 | 4/2005 |
| WO | WO 2004/007098 | 1/2004 |
| WO | WO 2005/120355 | 12/2005 |

OTHER PUBLICATIONS

2004 IEEE Ultrasonics Symposium: CMUTs with Dual Electrode Structure for Improved Transmit and Receive Performance pp. 501-504.

International Search Report dated May 29, 2007 issued in corresponding application No. PCT/2006/000285.

* cited by examiner

230

231

232

233

LF1-aperture

HF-aperture

DUAL FREQUENCY BAND ULTRASOUND TRANSDUCER ARRAYS

CROSS REFERENCE TO RELATED APPLICATIONS

This application is a continuation-in-part of U.S. patent application Ser. No. 11/493,283 which was filed with the U.S. Patent and Trademark Office on Jul. 26, 2006. This application claims the benefit of U.S. Provisional Application Nos. 60/702,423, filed Jul. 26, 2005; 61/010,545, filed Jan. 9, 2008; 61/011,006, filed Jan. 14, 2008. The entire content of each of U.S. application Ser. No. 11/493,283, U.S. Provisional Application No. 60/702,423, and U.S. Provisional Application No. 61/011,006 are incorporated herein by reference.

BACKGROUND OF THE INVENTION

1. Field of the Invention

The present invention is directed to efficient acoustic (sonic and ultrasonic) bulk wave transducers for operation in at least two frequency bands. Applications of the transducers are for example, but not limited to, medical ultrasound imaging, nondestructive testing, industrial and biological inspections, geological applications, and SONAR applications.

2. Description of the Related Art

The utilization of the nonlinear elasticity of tissue and ultrasound contrast agent micro-bubbles in medical ultrasound imaging provides improved images with less noise. The widest use is in the so-called harmonic imaging, where the $2^{nd}$ harmonic component of the transmitted frequency band is used for the imaging, extracted from the signal either through filtering or through the Pulse Inversion (PI) technique. A use of $3^{rd}$ and $4^{th}$ harmonic components of the transmitted pulse for imaging is also presented in U.S. Pat. No. 6,461,303.

U.S. Patent Application Publication No. 2005/0277835 and U.S. Patent Application Publication No. US 2006/0052699 A1 describe in depth different uses of dual band transmitted ultrasound and acoustic pulse complexes that provide images with reduced noise, images of nonlinear scattering, and quantitative object parameters that greatly enhance the use of ultrasound and acoustic imaging. The methods are applicable both with transmission and scatter imaging. For these applications, dual band pulse complexes are used, such as, for example, illustrated in FIGS. 1a and 1b. In FIG. 1a a high frequency (HF) pulse 101 rides on the peak pressure of a low frequency (LF) pulse 102. FIG. 1b shows another situation where the HF pulse 103 rides on the maximal gradient of the LF pulse 102. The ratios of the center frequencies of the LF and HF pulses are typically in the range of 1:5-1:20, and at the same time the HF pulse must be found in defined intervals of the LF pulse throughout defined depth ranges of the images.

In other applications, the same probe is required to transmit a low frequency wave (e.g., 0.5-2 MHz) for treatment of tissue (hyperthermia or cavitation destruction of tissue) or release of drug carried in nano or micro particles or bubbles, while being able to provide ultrasound imaging from the same probe surface at a higher frequency (e.g. 5-10 MHz). In yet another application, a probe is required for combined ultrasound treatment and imaging with 3 frequency bands, where a $2^{nd}$ lower frequency (LF2) band ~400 kHz is used, for example, to generate pulses for cavitation in the tissue to break nano-sized liposome particles containing drugs for drug delivery to tumors, a $1^{st}$ low frequency (LF1) band ~3 MHz is used for heating of the tissue for hyperthermia treatment of tumors (often referred to as HIFU—High Intensity Focused Ultrasound) or to increase blood flow in the tumor for improved oxygenation of the tumor or to improve the efficiency of the ~400 kHz breaking of drug carrying particle, and a high frequency (HF) band ~20 MHz is used for imaging, potentially also in combination with the ~3 MHz LF1 band for nonlinear manipulation of object elasticity for imaging, for example according to U.S. Patent Application Publication No. 2005/0277835 and U.S. Patent Application Publication No. US 2006/0052699 A1.

In yet other applications, a larger selection of frequency bands is required to be available for imaging from the same probe for a large variation of depth ranges. For example in portable ultrasound imaging systems for emergency medicine, center frequencies of 2.5 MHz are used for deep object imaging, and the same probe should be able to image at 7-10 MHz center frequencies for objects closer to the body surface. The arrays can for example be arranged as phased linear arrays, switched linear arrays, and curvilinear arrays. The need for multiband transducers is also found in many other applications of acoustic imaging such as, for example, in non-destructive testing (NDT) of materials, observations of geological formations with elastic waves, and SONAR measurements and imaging of fish, for example close to the sea bottom, the sea bottom, and objects like mines both on the sea bottom and buried under the sea bottom or in the soil on land. This both relates to nonlinear measurements and imaging with multiband pulse complexes, and the ability to select different frequency band pulses for different needs, such as different measurement ranges.

Dual band transmitted pulses were used in M-mode and Doppler measurements in Br Heart J. 1984 January; 51(1): 61-9. Further examples are shown in U.S. Pat. No. 5,410,516 where sum and difference bands of the transmitted bands produced in the nonlinear scattering from contrast agent micro-bubbles where detected. A further development of this dual band transmission is done in U.S. Pat. No. 6,312,383 and U.S. patent application Ser. No. 10/864,992.

SUMMARY OF THE INVENTION

An object of the current invention is to provide solutions for meeting the above-referenced challenges of transducer array designs. We do in the description most often consider the situation where the elastic waves are in the ultrasound frequency range, but it should be clear to anyone skilled in the art that the solutions according to the invention can be applied to any frequency range of acoustic waves, and also to shear waves in solids.

This summary gives a brief overview of components of embodiments of the invention and does not present any limitations as to the extent of the present invention, where the present invention is solely defined by the claims appended hereto.

The presents invention presents solutions to the general need for an acoustic array probe that transmits/receives acoustic pulses with frequencies in separated multiple frequency bands through an at least partially common radiation surface. The acoustic pulses may, for example, be ultrasound pulses. The advantages of the common radiation surface include minimizing the size of a dual or multi band probe to be used from the same instrument. In other situations one needs a common radiation surface for simultaneous transmission of a high frequency (HF) and a low frequency (LF1) pulse with low or controllable phase sliding between the HF and LF1 pulses in an actual imaging range, so that the HF pulse is found in a defined region of the LF1 pressure oscillation.

The invention also presents a general procedure to design an array with a freely selectable number of operating frequency bands. More specifically, the invention presents solutions to transducer arrays for transmission and reception of 3-band pulse complexes containing a high frequency (HF), a $1^{st}$ lower frequency (LF1) and a $2^{nd}$ lower frequency (LF2) band, or transmission and potential reception of separate pulses in 3 different frequency bands (HF, LF1, and LF2 bands). The invention further provides solutions where the ratios of the center frequencies are in the range (HF:LF1) of ~3:1-20:1, with no defined upper or lower limit to the ratio. The ratio of the center frequencies of the LF1:LF2 bands can have similar values. With the lowest separation of the center frequencies, a probe for multi-selection of image frequency bands, for example center frequencies as 2 MHz, 5.5 MHz, and 15 MHz, is achievable. With a larger separation of the center frequencies, a probe for imaging with the methods described in U.S. Patent Application Publication No. 2005/0277835 and U.S. Patent Application Publication No. US 2006/0052699 A1, that also can include frequency bands for HIFU and cavitation treatment of the tissue, is obtained.

To achieve transmission of multi-band pulses where at least a part of the radiation surfaces are common, the invention presents solutions with a group of arrays that are resonant for each frequency band, and that has at least partially a common radiation surface. The arrays may have a general arrangement of the elements, for example linear phased or switched arrays, or annular arrays. The arrays can be flat or curved, both concave and convex, in one or two dimensions. Element divisions of the linear arrays in the elevation direction to for example a 1.5D, a 1.75D and even a full 2D array are also embodiments according to the present invention. Further, different sizes, forms, and divisions of the array elements for the different bands such as, for example, but not limited to, an annular array for low frequency treatment pulses with a linear switched or phased array for imaging, are also possible. The present invention also provides solutions for efficient packaging of electronics related to the array beam forming, such as transmit and receive amplifiers for the individual array elements, sub-aperture beam former electronics that allow connection of a group of elements to the instrument via a single wire, electronic switches for connecting selected groups of array elements in electric parallel to beam former channels via a single wire, both for transmit and receive.

To minimize relative position sliding between the different frequency band pulses with depth and to defeat diffraction to obtain adequately collimated low frequency (LF1, LF2, . . . , LFn, . . . ) beams at deep ranges, the present invention presents a solution where the arrays for the different bands have a large common radiation surface, and where parts of the radiation surfaces of the lower frequency arrays can be outside the radiation surfaces of higher frequency arrays. To minimize the overlap between the different frequency band pulses in the near field, the present invention also presents solutions where central parts of the lower frequency apertures are inactive. To efficiently select between different sizes and overlaps of the radiation surfaces of the different bands, different arrays are used for the different bands, with special solutions of the array constructions to provide common radiation surfaces of the different bands.

In one embodiment according to the present invention, the HF and LF1 pulses are generated with separate piezoelectric layers stacked in front of each other with the HF piezo-layer in the front, and an isolation section for HF vibrations to the front of the LF1 piezo-layer, to obtain a common HF and LF1 array radiation surface. A load matching section of impedance matching layers is placed between the HF piezo-layer and the load material to the front. The isolation section is designed so that the reflection coefficient between the HF piezo-layer and the isolation section is high in the HF band so that the layers behind the HF piezo-layer has low influence on resonances in the electro-acoustic transduction of the HF piezo-layer in the HF band. The isolation section is also designed so that in the LF1 band it cooperates with the probe layers in front of the isolation section to provide acoustic matching of the LF1 piezo-layer to the load material.

Close to unit reflection coefficient between the HF piezo-layer and the isolation section is obtained when the impedance seen into the isolation section from the front is low or high compared to the characteristic impedance of the HF piezo-layer. When the impedance into the isolation section from the front is low in the HF band, the HF piezo-layer will have a thickness resonance when it is approximately half a wavelength thick around the center of the HF band. When the impedance into the isolation section from the front is high in the HF band, the HF piezo-layer will have a thickness resonance when it is approximately a quarter wavelength thick around the center of the HF band. The quarter wave resonance generally allows wider bandwidth of the HF layer resonance, but with poorer phase angle of the electrical impedance compared to for half wave length resonance of the HF piezo-layer.

The present invention provides special designs of the isolation section that provide either adequately high or adequately low impedance into the front of the isolation section in the HF band, with low sensitivity to the impedance seen from the back of the isolation section. This is especially important when the LF1 piezo-layers are made as ceramic/polymer composites where variations in the reflection coefficient from the HF layer towards the isolation section should be minimized when the isolation section connects to polymer or ceramics in the composite. To achieve this reduced impedance sensitivity of the reflection coefficient, the present invention provides solutions where the isolation section is composed of at least two acoustic layers.

In one embodiment of the isolation section according to the present invention, the isolation section contains an impedance regularizing layer at the back of the isolation section that is adequately thin and heavy so that in the HF band the isolation section approximately represents a mass, adequately large, in series with the impedance to the back. This mass is then in series with the loading of the isolation section to the back, and makes the impedance transformation of the whole isolation section less dependent on whether the isolation section ends into polymer or ceramic in the LF1 piezo-composite. The impedance regularizing layer is preferably a heavy material such as, for example, Cu, Ag, Au, Pd, Pt, W, or alloys of such materials, or powders of such materials or their alloys sintered together or glued in a solvent such as a polymer. The thickness of the back layer can typically be of the order of $\lambda_{HF}/30$ or higher. Due to the large wave propagation velocity of Si (8.44 mm/μsec), a Si layer can also be used for an impedance regularizing layer with adequate mass, although the mass density of Si is only 2330 kg/m$^3$. The present invention also presents an embodiment where the impedance regularizing layer of the isolation section is made of ceramics, where the ceramics layer can be part of the LF1 piezo-layer. This ceramics back layer may conveniently be combined with a thin layer (the order of $\lambda_{HF}/30$) of heavy material such as Cu, Ag, Au, Pd, Pt, W, or alloys of such materials, or powders of such materials or their alloys sintered together or glued in a solvent such as a polymer.

A low impedance into the isolation section can then for example be obtained with a matching layer in front of said impedance regularizing layer of large mass, where said matching layer has low characteristic impedance and is quarter wavelength thick around the center of the HF band. The matching layer can preferably be made of polymer or similar material. An approximation for matching the LF1 piezo-layer to the load in the LF1 band is realized by assuming that both the isolation section matching layer and the HF piezo-layer with load matching layers will be thin compared to the wavelength in the LF1 band. This allows a thin layer approximation where said low impedance matching layer behaves as an elastic spring in series with the mass of the HF piezo- and matching layers and the load impedance. The center frequency of the LF1 band is then selected at the resonance between this spring and mass where the phase of the impedance into said isolation section matching layer seen from the back is zero. This resonance frequency can be tuned by varying the stiffness of said isolation section matching layer and the mass of the HF piezo and load matching layers. The mass may, for example, be tuned by varying the ceramic volume fill in the HF piezo-composite.

The above-described embodiment can be modified to obtain a high impedance into the isolation section by adding a second $\lambda_{HF}/4$ matching layer with high characteristic impedance that connects to the HF piezo-layer in front of the first $\lambda_{BF}/4$ matching layer with low characteristic impedance. With this solution, the impedance seen from the front into the isolation section is less dependent on the thin impedance regularizing layer described above, where this layer in many situations can be removed when two $\lambda_{HF}/4$ matching layers are used. The selection of characteristic impedances of the first and second matching layers may be done through standard considerations of impedance matching known to those skilled in the art. In the LF1 band the first (low impedance) matching layer will then behave approximately as a spring in series with the combined mass of the second (high impedance) matching layer and the HF piezo- and load matching layers, where the center frequency of the LF1 band is selected at the resonance frequency of said spring and load system, where the material parameters of the spring and mass system can be tuned for resonance in the LF1 band.

In a less efficient embodiment, a single $\lambda_{HF}/4$ matching layer with high characteristic impedance to the front of the impedance regularizing layer of large mass may be used to provide high impedance into the isolation section in the HF band. In the LF1 band this single matching layer will approximately behave as a mass in series with the mass of HF piezo- and load matching layers and provide a load impedance seen from the LF1 piezo-layer that has an inductive phase. While this embodiment does not provide optimal impedance matching, a useful form of the LF1 electro-acoustic transfer function is nevertheless obtained.

The above examples provide some specific examples of the isolation section when two layers are used according to the present invention. However, the present invention is not meant to be restricted to the specific examples of two layers. The impedance regularizing mass layer is very useful when the LF1 piezo-layer is made as a ceramic polymer composite, but can be omitted when the LF1 piezo-layer is made as a whole ceramic. This can for example be the situation when the LF1 layer is used for high power therapy purposes without direction steering of the beam.

According to the present invention, second and third or more lower frequency bands may be added to the structure above by extending the piezo-layer structure backwards in front of the backing with sections containing an isolation section in front of a piezoelectric layer for each new low frequency band, where the resonance frequency for the piezo-layers has a monotone decrease with the position backwards in the structure. The isolation sections are designed according to the same principles as for the dual piezo-layer structure described above, where the reflection coefficient into the front of the isolation section is close to unity within the resonance band of the neighbor piezo-layer in front of said new section. Within the resonance frequency of said new piezo-layer, the new isolation section interacts with the layers in front of the isolation section to provide resonant impedance matching between the load and the new piezoelectric layer. The structure can hence be extended backwards with a new such combined isolation section and piezo-layer for each new lower frequency band, in principle ad infinitum, where most practical applications requires in total 2 or 3 lower frequency bands in addition to the HF band.

The structure typically ends with a backing material that has so high absorption that reflected waves in the backing material can be neglected. The last piezo-layer can attach directly to the backing material, or through back matching sections composed of impedance matching layers. The backing material can be used as acoustic power absorbant to reduce resonances in the electro-acoustic transfer functions. Resonances in any of the frequency bands can also be dampened with matching layers of absorbing materials, for example viscous damping polymer materials, and even adding particles to the polymer materials to increase absorption. Viscous damping polymer materials and particle filled polymer materials can also be used in the polymer fills of the ceramic/polymer composites of the piezoelectric layers. Solid/polymer composites can also be used for matching layers to tune the characteristic impedance, where viscous and/or particle filled polymers can be used for increased absorption in the matching layers.

Heavy layers or high-impedance layers of said isolation sections can conveniently be made of one or more electronic substrate layers (typically Si-layers) with electronic circuits so that groups of array elements can be connected to further processing, within the probe or in the instrument, via a reduced number of wires. The electronic circuit may, for example, include transmit and receive amplifiers for the array elements, channel number reducing circuits such as switches for electronically selectable connection of groups of array elements in electric parallel to beam former channels, and/or sub-aperture beam forming for one or both of transmit and receive. The signals from groups of elements or groups of sub-apertures of elements may also be transmitted on a single wire by time-multiplexing samples of the signals from such groups, where the time-multiplexing circuits are integrated into the electronic substrate layers, to reduce the cable connections to the arrays.

The electronic substrate layers may be part of the heavy, impedance regularizing back layer of an isolation section, or alternatively part of a high impedance front layer of an isolation section. In the latter case, electronic circuits on the front of the substrate layer may connect directly to the array elements in front such as, for example, HF array elements. Such connections may be realized through metal pads and other known and hereafter developed connection techniques such as anisotropic conducting polymer glue containing conducting particles, micro soldering, ultrasonic bonding. Channel number reducing circuits are conveniently implemented in these front electronic substrate layers (e.g., switched element selection, sub-aperture electronics), to reduce the number of connections required to further processing electronics that can comprise or be part of an impedance regularizing back layer of an isolation section. Such reduced number of connections through a matching layer with low electrical conduction can then be obtained via metal connectors through the layer that are so thin that they have minimal effect on the characteristic acoustic impedance of the matching layers. To extend the thickness of a back isolation section layer of Si substrates for increased processing and circuit complexity in these layers, the lower frequency array behind can conveniently be made as a ceramic/polymer composite with average characteristic acoustic impedance close to that of the electronic substrate (for Si substrate the characteristic impedance is approximately 19.7 MRayl) so that the electronic substrate layers participate in the definition of the resonance of said lower frequency array.

Substrate layers with electronics may also be placed in front of the HF array, behind the HF acoustic matching layers. With the front placement of the substrate layers, the HF array is conveniently made of piezo-ceramic/polymer composite with average characteristic impedance close to that of the electronic substrate layer, so that the substrate layers participate in the resonance definition of the HF array.

In a further embodiment according to the present invention to obtain common HF and lower frequency array radiation surfaces, the HF transduction is provided by vibrating membranes on a substrate activated by cmut/pmut technology, while the lower frequency pulses are generated with a piezo-layer to the back of said cmut/pmut structure. Several electronic substrate-layers may be conveniently placed behind the cmut/pmut substrate. These electronic substrate-layers may, for example, include transmit and receive amplifiers, electronic switches, sub-aperture beam forming circuitry. The high acoustic propagation velocity of Si (8.44 mm/µsec), allows the total thickness of such layers to be a fraction of the LF1 wave length in Si, and thus provide minimal modification of the lower frequency transmission through the Si layers. Such modification is further reduced by making the lower frequency piezo-layer closest to the substrates as a ceramic/polymer composite with characteristic impedance close to that of the electronic substrate layers. The structure may be extended backwards with more piezoelectric layers with resonances in lower frequency bands (LF2, LF3, . . . ) including isolation sections for vibrations within the bands of the layers to the front, according to the principles of the invention described above.

In yet another embodiment according to the present invention, both the HF and the LF1 pulses are generated with separate cmut/pmut membranes on a common substrate, either side by side of each other or the HF membranes on top of the LF1 membranes, to obtain common HF and LF1 array radiation surfaces. The HF LF1 membranes are then optimized for operation in their respective frequency bands. In yet a further embodiment according to the present invention, both the HF and more than one lower frequency bands are generated with different cmut/pmut membranes for the different frequency bands on a common substrate to obtain common array radiation surfaces for a HF band and more than one lower frequency bands. The membranes for the different frequency bands may be placed side by side of each other. Alternatively, some or all of the membranes may be stacked on top of others with increasing frequency band from the lowest to the top, while the rest of the membranes are placed directly on the substrate by the side of the stacked membranes. Also in these embodiments one can conveniently place several electronic substrate-layers with transmit and receive amplifiers and beam forming circuitry behind the cmut/pmut substrate, and the structure can be extended backwards with added lower frequency piezo-layers with isolation section in front, as described above.

These arrays can be used for transmission and reception in each of the frequency bands. The methods cited in U.S. Patent Application Publication No. 2005/0277835 and U.S. Patent Application Publication No. US 2006/0052699 A1 would transmit dual band complexes and use only the received signal in the highest frequency band for processing to measurement or image signals. The frequency bands of the transmitted dual band complex can then be selected from any of the frequency bands in the probe.

The invention is also useful with sparse arrays, where the grating lobes from the HF aperture should be different from possible grating lobes of the lower frequency arrays, to suppress the effect of transmitted HF grating lobes for example with imaging methods and instruments according to U.S. Patent Application Publication No. 2005/0277835 and U.S. Patent Application Publication No. US 2006/0052699 A1.

The present invention relates to instruments that uses acoustic multiple band array probes according to the invention for different purposes such as, for example, the use of the different frequency bands of the probe for imaging at different depths, acoustic tissue treatment at different frequencies, or imaging according to the methods described in U.S. Patent Application Publication No. 2005/0277835 and U.S. Patent Application Publication No. US 2006/0052699 A1, or combined acoustic treatment and imaging with any method. The frequency bands are selected by the instrument, either automatically from the operational settings of the instrument, or manually by the instrument operator through instrument controls. For example, the radiation surfaces of the lower frequency apertures may be selectably varied to be one of equal to the HF transmit aperture and larger than the HF aperture where the HF radiation area is part of the lower frequency radiation areas, and the LF1 and/or the HF apertures can be selected to have an inactive central region, in accordance with the imaging methods described in U.S. Patent Application Publication No. 2005/0277835 and U.S. Patent Application Publication No. US 2006/0052699 A1.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views.

DETAILED DESCRIPTION OF THE PRESENTLY PREFERRED EMBODIMENTS

Figure 1A:
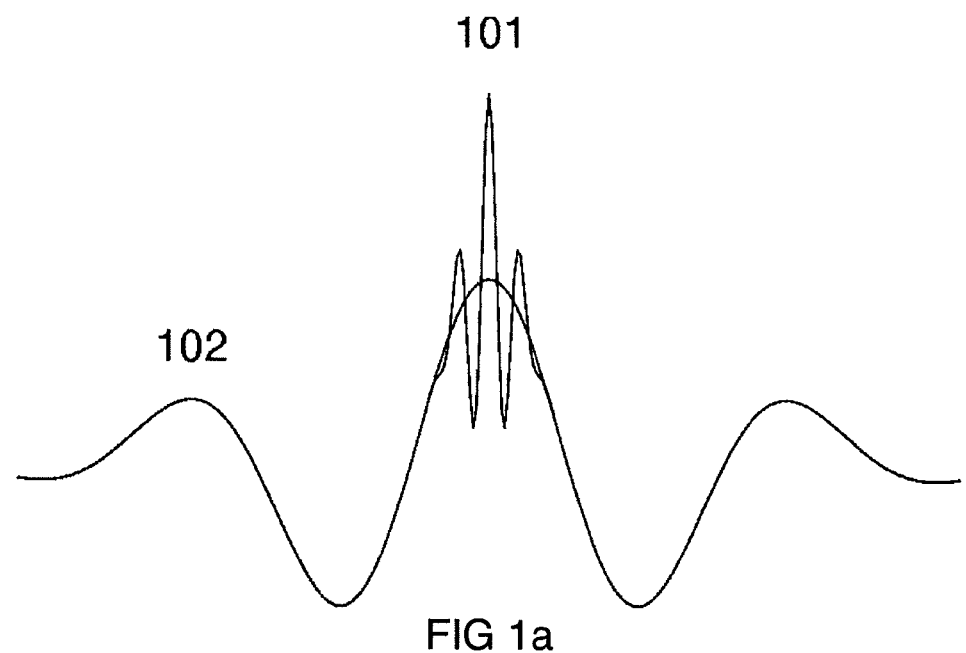
FIGS. 1a and 1b show examples of low frequency (LF1) and high frequency (HF) pulse complexes to be transmitted.
Figure 1B:
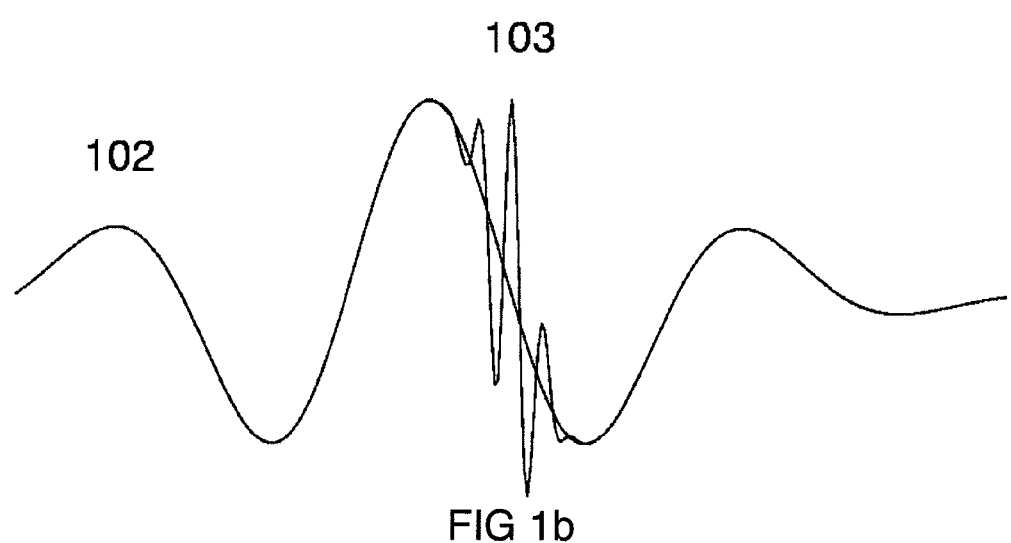

Example embodiments of the invention will now be described in relation to the drawings. Embodiments including dual frequency arrays are first described and the principles described therein are then extended to three or more frequency bands. Typical examples of dual frequency pulses to be transmitted are shown in FIGS. 1a and 1b as described above. The challenges in the design of the arrays lie both in the design of the radiation surfaces so that the HF pulse is kept within desired location of the LF1 pulse for adequate image range while maintaining adequate amplitude of the LF1 pulse, and in design of a vibration structure that allows transmission of LF1 and HF pulses with such wide separation between the frequencies from the same surface.

In some of the applications, the amplitude of the LF1 pulse at the location of the HF pulse is required to be as high and close to constant as possible throughout an adequate imaging range. This may require large apertures of the LF1 radiation surface to avoid diffraction spread of the LF1 beam due to the long wavelength of the LF1 pulse compared to the HF pulse. The width of the HF transmission aperture may be limited by a requirement on the length of the HF transmit focal region. This gives situations where one would prefer a larger LF1 aperture than the HF aperture, which introduces a sliding between the position of the HF pulse relative to the LF1 pulse.

Figure 2A:
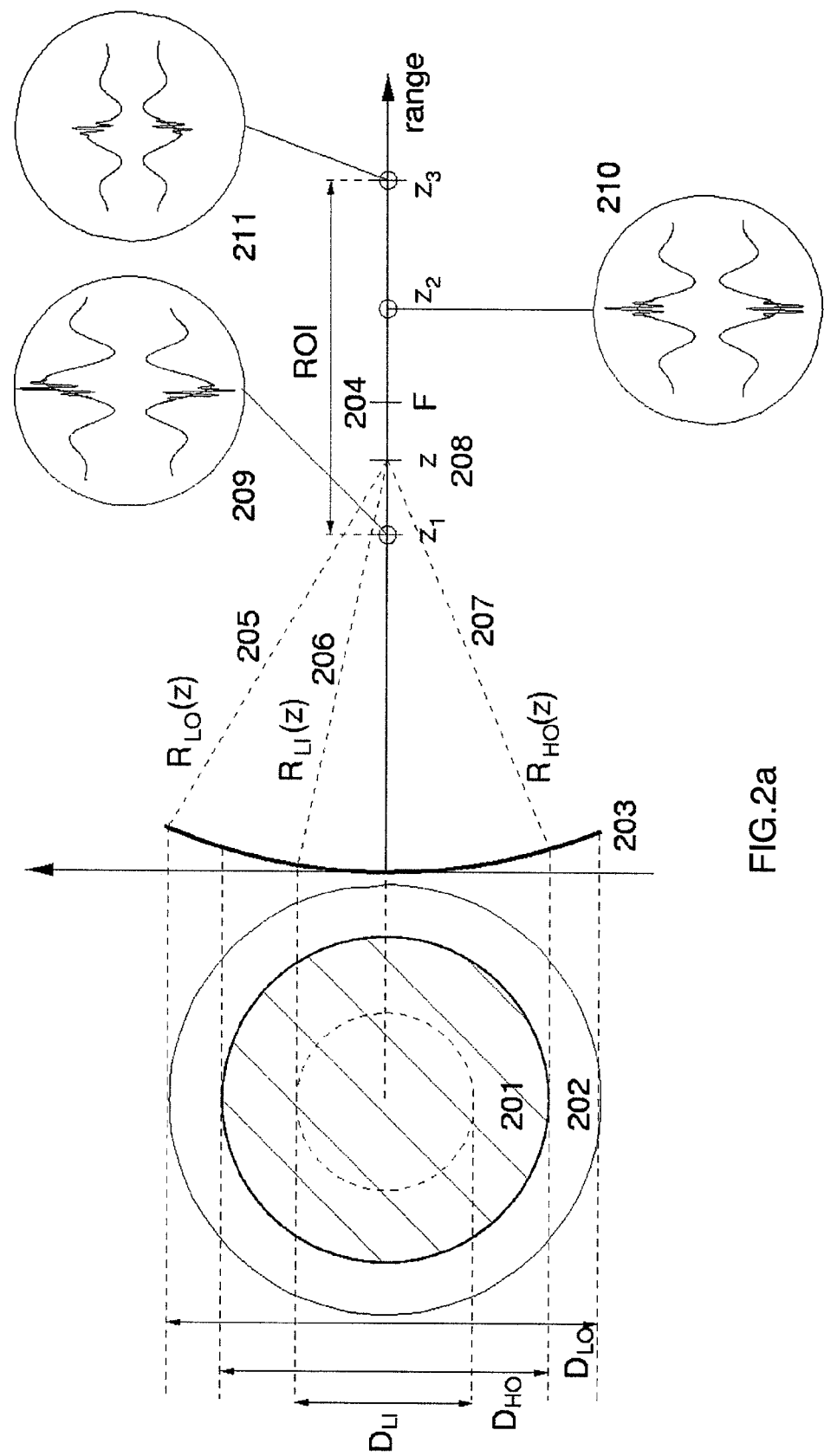
FIGS. 2a, 2b, 2c, and 2d show example HF and LF1 radiation surfaces according to embodiments of the present invention, and also for analysis of HF and LF1 pulse phase relationships.

For further analysis of this sliding phenomenon we consider circular apertures because we have analytic expressions of the field on the axis of such apertures. FIG. 2a shows by way of example a circular HF transmit aperture 201 with diameter $D_{HO}=2a_{HO}$ and a concentric LF1 transmit aperture 202 which for the example is shown as a ring with outer diameter $D_{LO}=2a_{LO}$ and inner diameter $D_{LI}=2a_{LI}$. The cross section view in FIG. 2a shows the HF and LF1 transmit apertures as 203. The HF and LF1 transmit apertures in this embodiment are curved to the same focus F, 204. In other situations, the HF and LF1 transmit apertures may have different foci, where the LF1 aperture also can be unfocused. The transmitted axial continuous wave field for the LF1 and the HF apertures at a frequency $\omega$ is as a function of the axial distance z given as $$\begin{aligned}P_{LF}(z,\omega) &= \frac{F}{z}\frac{e^{-ikR_{LI}(z)}-e^{-ikR_{LO}(z)}}{F/z-1}P_{L0}(\omega) \quad &\text{a)}\\ &= i2e^{-ik(R_{LO}(z)+R_{LI}(z))/2}\frac{F}{z}\\ &\quad \frac{\sin k(R_{LO}(z)-R_{LI}(z))/2}{F/z-1}P_{L0}(\omega)\\ P_{HF}(z,\omega) &= \frac{F}{z}\frac{e^{-ikR_{HI}(z)}-e^{-ikR_{HO}(z)}}{F/z-1}P_{H0}(\omega) \quad &\text{b)}\\ &= i2e^{-ik(R_{HO}(z)+R_{HI}(z))/2}\frac{F}{z}\\ &\quad \frac{\sin k(R_{HO}(z)-R_{Hi}(z))/2}{F/z-1}P_{H0}(\omega)\end{aligned} \quad (1)$$

where $k=\omega c$ and $\omega$ is the angular frequency of the transmitted pulse and c is the acoustic propagation velocity. $R_{LO}(z)$ shown as 205 is the distance from the outer edge of the LF1 aperture to the point z (208) on the z-axis, $R_{LI}(z)$ shown as 206 is the distance from the inner edge of the LF1 aperture to 208 on the z-axis, and $R_{HO}(z)$ shown as 207 is the distance from the outer edge of the HF aperture to 208 on the z-axis, and $R_{HI}(z)$ is the distance from the inner edge of the HF aperture to 208 on the axis. As the HF aperture has no missing part in the center, we get $R_{HI}(z)=z$, but we shall also consider situations where a central part of the HF aperture with diameter $D_{HI}=2a_{HI}$ is missing.

$P_{LO}(\omega)$ is the LF1 transmit pressure at the aperture while $P_{HO}(\omega)$ is the HF transmit pressure at the aperture. An absorbing medium may be modeled by a complex wave vector $k=k_r(\omega)-ik_d(\omega)=\omega/c_p(\omega)-i\alpha\omega$, where the imaginary part $-k_d$ represents power absorption and the real part $k_r$ represents wave propagation with an in general frequency dependent phase velocity $c_p(\omega)$. The frequency variation of the phase velocity is produced by the absorption, and may for most situations in tissues and materials with similar absorption be neglected, i.e., $c_p(\omega)\approx c$. The absorption coefficient is often, due to multiple relaxation phenomena, proportional to the frequency, i.e., $k_d(\omega)\approx\alpha\omega$.

We note from the first lines of the expressions in Eqs. (1a) and (1b) that the pressure in the near field breaks up into two pulses with delays $R_{LI}(z)/c$ and $R_{LO}(z)/C$ for the LF1 pulse, and $R_{HI}(z)/c$ (from the center) and $R_{HO}(z)/c$ for the HF pulse. As z increases, the delay difference between these pulses reduces, so that the two pulses start to interfere, both for the LF1 and HF waves. We then get a longer pulse than given by $P_{LO}(c)$ and $P_{HO}(c)$ with complex central part due to interference between the edge pulses. The interference can introduce zeros in the middle of the LF1 and HF pulses with destructive interference, and maxima with constructive interference. For $z<F$, the propagation distance to z on the axis from the outer edge is longer than the propagation distance from the inner edge. Thus, for an absorbing medium, one does not obtain complete destructive interference with zeros of the central part of the LF1 and HF pulses. Apodization of the pressure drive amplitude across the array surface, so that the drive amplitude is reduced towards the edges, will also reduce in amplitude the pulses from the edges, i.e., with the delay $R_{LO}(z)/C$ for the LF1 pulse, and $R_{HO}(z)/c$ for the HF pulse.

In the focal region, Taylor expansion of the second lines of Eqs. (1a) and (1b) shows that interference between the two pulses produces a pulse which approaches the time derivative of the transmitted pulses $P_{LO}(c)$ and $P_{HO}(c)$ in the focus, and with a delay given by the phase terms. This situation is also found in the far-field of an unfocused aperture, and generally relates to the region where the beam width is limited by diffraction. The phase terms in Eqs. (1a) and (1b) represent the average propagation lag from the LF1 and HF apertures, respectively as $$\tau_{LF}(z) = \frac{1}{2c}(R_{LO}(z) + R_{LI}(z)) \quad (2)$$

$$\tau_{HF}(z) = \frac{1}{2c}(R_{HO}(z) + R_{HI}(z))$$

The differentiation of the transmitted LF1 pulse $P_{LO}(c)$ towards the focus produces an added time advancement of $T_{LF}/4$ of the LF1 pulse oscillations, where $T_{LF}$ is the temporal period of the LF1 pulse center frequency, with minor effect on the pulse envelope. Thus, in the focal region, the LF1 and HF pulse lengths are given by the transmitted pulse lengths on the array surface, with a change in the oscillation phase of 90 deg due to the differentiation and propagation lags given by Eq. (2). Due the differentiation of the LF1 pulse, and in addition when $D_{LO}>D_{HO}$, HF and LF1 pulses will get z-dependent propagation delays that differ from each other, and the location of the HF pulse relative to the LF1 pulse will slide with depth as exemplified at points 209-211 for depths z1, z2 and z3 in FIG. 2a.

Although the above formulas are developed for circular apertures, they illustrate a general principle for apertures of any shape because the radiated beam originates as interference between spherical waves with origin at all points on the aperture (Huygen's principle). Hence, the waves originating from points on the LF1 aperture outside the HF aperture, will have longer propagation distance to the axis than points on the HF aperture. The difference between these propagation distances varies with depth z, which hence produces the position sliding between the HF and the LF1 pulse.

We see that when the LF1 and HF transmit apertures are equal, there is no sliding between the LF1 and HF pulses in the focal region, but we get a $T_{LF}/4$ advancement of the LF1 pulse oscillations from the near field to the focus, due to the temporal differentiation of the LF1 pulse in the diffraction limited region. An LF1 transmit aperture equal to the HF transmit aperture can in many situations be too small so that too high LF1 beam divergence due to diffraction is found. Therefore, it is often desirable to have a wider LF1 transmit aperture than the HF transmit aperture. This produces some added sliding between the HF and LF1 pulses with depth, which can be established between tolerable limits through the dimensioning of the transmit apertures. This sliding can also be utilized for different purposes, for example to compensate for variations in the LF1 pulse amplitude so that the observed LF1 pressure at the location of the HF pulse has less variation with depth than the LF1 pulse amplitude.

To further analyze the situation when the LF1 and HF apertures are different we continue with the circular apertures. For a common focal depth F, we get the distances from outer and inner edges of the LF1 and HF apertures as $$R_{gO}(z) = \sqrt{z^2 + 2e_{gO}(F-z)} \quad (3)$$

$$e_{gO} = F - \sqrt{F^2 - a_{gO}^2} \approx \frac{a_{gO}^2}{2F}$$

$$g = L, H$$

$$R_{gI}(z) = \sqrt{z^2 + 2e_{gI}(F-z)}$$

$$e_{gI} = F - \sqrt{F^2 - a_{gI}^2} \approx \frac{a_{gI}^2}{2F}$$

$$g = L, H$$

where $D_{LO}=2a_{LO}$, $D_{LI}=2a_{LI}$, $D_{HO}=2a_{HO}$, and $D_{HI}=2a_{HO}$. When the last term under the root sign is relatively small, we can approximate $$R_{gO}(z) \approx z + \frac{F-z}{2Fz}a_{gO}^2 \quad (4)$$

$$R_{gI}(z) \approx z + \frac{F-z}{2Fz}a_{gI}^2$$

$$g = L, H$$

The z variation of the propagation lag difference between the LF1 and HF pulses is then found by inserting Eq. (4) into Eq. (2) which gives $$\Delta\tau(z) = \tau_{LF}(z) - \tau_{HF}(z) \quad (5)$$

$$= \frac{1}{2c_0}\frac{F-z}{2Fz}(a_{LO}^2 + a_{LI}^2 - a_{HO}^2 - a_{HI}^2)$$

Hence, by choosing $$a_{HO}^2 + a_{HI}^2 = a_{LO}^2 + a_{LI}^2 \quad (6)$$

we obtain, with accuracy within the approximation, zero sliding between the HF and LF1 pulses in the focal range of the LF1 pulse, even in the situation where the outer dimension of the LF1 transmit aperture is larger than the outer dimension of the HF aperture.

A disadvantage with the removed central part of the HF transmit aperture is that the side lobes in the HF transmit beam increase. However, these side lobes are further suppressed by a dynamically focused HF receive aperture. The approximation in Eq. (4) is best around the beam focus, and Eq. (6) do not fully remove phase sliding between the LF1 and HF pulses at low depths. For other than circular apertures (for example rectangular apertures) one does not have as simple formulas for the axial field as in Eq. (1) but the analysis above provides a guide for a selection of a HF transmit aperture with a removed center, for minimal phase sliding between the LF1 and the HF pulses with depth. With some two-dimensional arrays, one can approximate the radiation apertures with circular apertures where Eq. (6) can be used as a guide to define radiation apertures with minimal phase sliding between the LF1 and HF pulses.

Different measurement situations put different requirements on tolerable variations of the LF1 amplitude and also position sliding between the HF and the LF1 pulses. Accordingly, it is desirable for at least the LF1 transmit aperture to be composed of elements so that the effective width of the LF1 transmit aperture can be selected together with the relative transmit timing of the HF and LF1 pulses so that in the desired range the best possible amplitudes and relative locations of the two pulses are achieved. The present invention provides an instrument using such a probe, where the selection of the active LF1 transmit aperture surface may be done automatically by the instrument depending on the application (e.g., suppression of multiple scattering noise or detection of contrast agent micro bubbles) and image depth, or manually by the instrument operator. It may also be desirable to vary the HF transmit aperture. Further, during reception of the scattered HF signal a receive aperture that increases dynamically with the focus to follow the scatterer depth is desired. Hence, a preferred solution is a combined LF1 and HF array with common radiation surfaces, but where the actual LF1 and HF transmit apertures can be selected for the application, where the LF1 transmit aperture is typically larger than the HF transmit aperture, while the HF receive aperture can be selected wide or possibly wider than the LF1 transmit aperture at large depths, for example with dynamic receive aperture with depth.

Figure 2B:
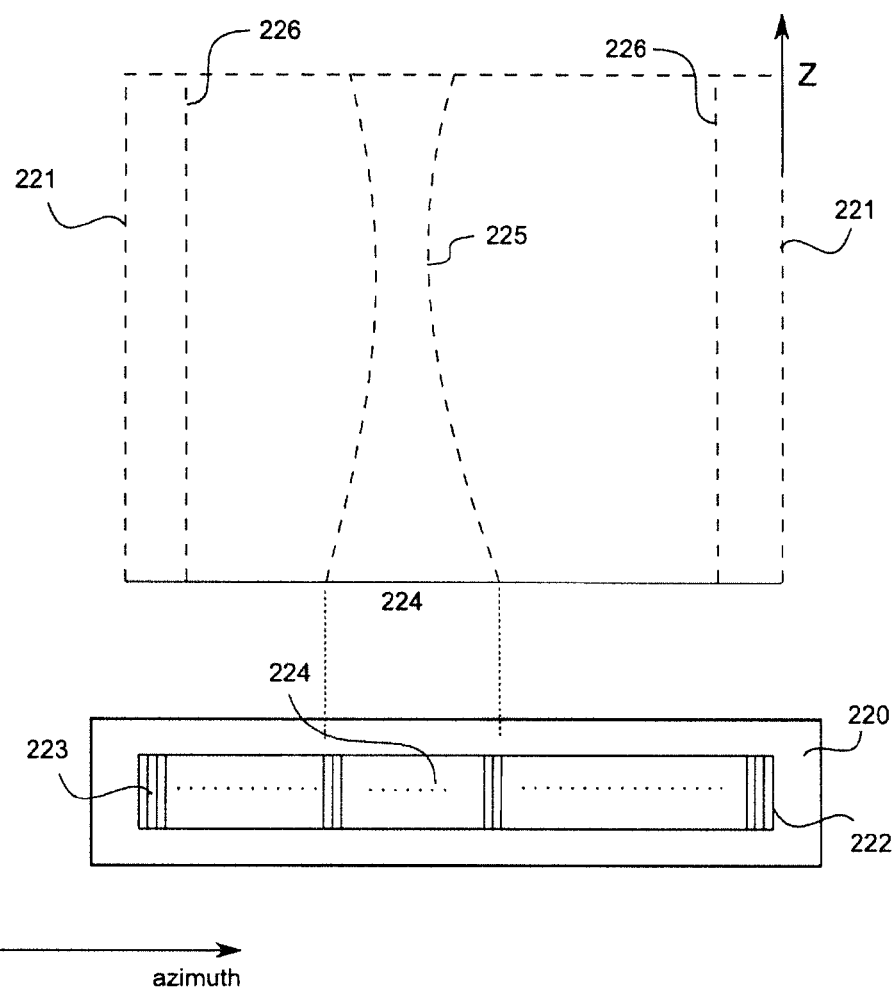

In the above-described example, the LF1 and HF transmit amplitudes have common foci, which is an advantage in some situations, but differences in LF1 and HF transmit foci can also be utilized in the beam designs for different purposes. For example, a LF1 array that is flat outside the HF aperture, and has the same curvature or lens focus as the HF array within the HF aperture, may be used for practical purposes. For some applications an unfocused LF1 aperture that is so wide that the actual imaging range is within the near-field region of the LF1 aperture may be used to avoid phase changes of the LF1 pulse due to the differentiation of the LF1 pulse as one moves into the diffraction limited region (far-field, focal region) of the LF1 beam. With a switched linear HF array where the HF beam directions are normal to the radiation surface (aperture), the LF1 aperture may for some applications be a single element array transducer with somewhat wider aperture than the linear HF array, so that the LF1 near field region covers the whole HF image range. FIG. 2b show such an arrangement. More specifically, FIG. 2b shows a single element LF1 array 220 that produces a beam illustrated in side view as 221 up to the maximal image depth Z, which is within the near field of the LF aperture. FIG. 2b further shows the front view of a radiating surface of a linear HF array 222 with linear array elements 223, where a selected group of the elements 223 produces a selected HF transmit aperture 224 that produces the HF transmit beam 225. For imaging the HF transmit and receive beams are scanned within a rectangular image field 226 while the LF1 beam covers the field 221 for all HF beams.

Figure 2C:
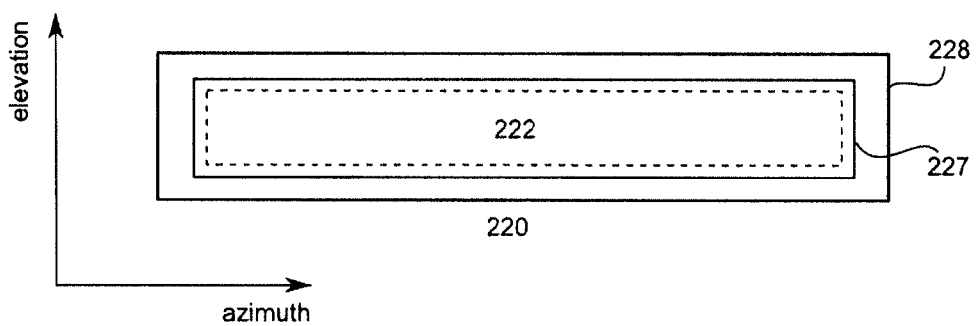

The embodiment in FIG. 2b is useful to obtain low variation of the LF1 pressure along the HF pulse propagation, which is useful for imaging of nonlinear scattering of microbubbles and hard scatterers, as described in U.S. patent application Ser. Nos. 10/189,350 and 10/204,350. However, for improved suppression of multiple scattering noise, for example as described in the same applications, it is useful to have an LF1 aperture that is inactive in a central region as indicated in FIG. 2c. In FIG. 2c the LF1 array 220 includes two elements, i.e., a central element 227 and an outer element 228. In this embodiment the central element is larger than the HF array 222. However, in other applications the element 227 may be narrower than the HF array 222 in the elevation direction. For imaging of nonlinear scattering, the two LF1 elements 227 and 228 would typically be coupled electrically in parallel to give an active LF1 transmit array 220 as in FIG. 2b. For improved suppression of HF multiple scattering noise only the outer element 228 is used for transmission of the LF1 pulses, which would reduce the nonlinear interaction between the HF and LF1 pulses in the HF near field.

Figure 2D:
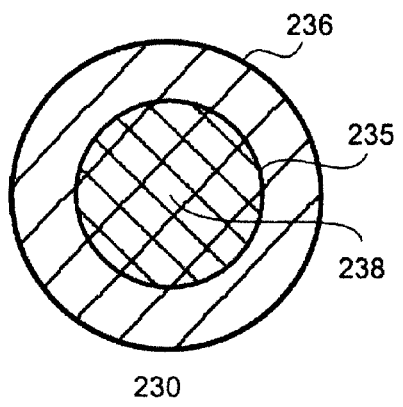
Figure 2D:
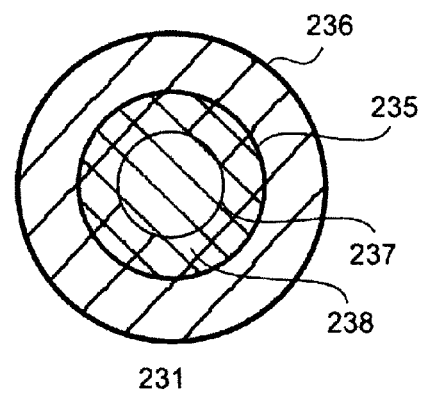
Figure 2D:
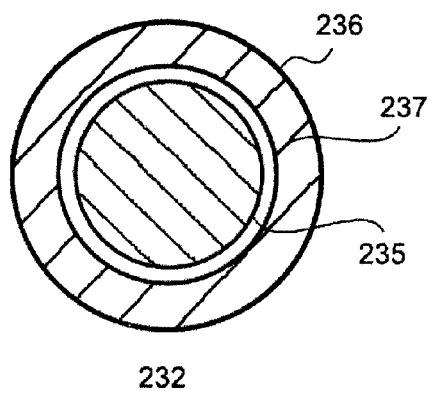
Figure 2D:
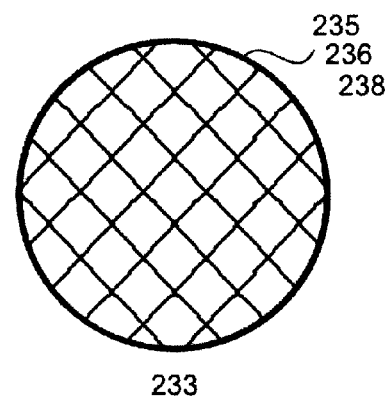
Figure 2D:
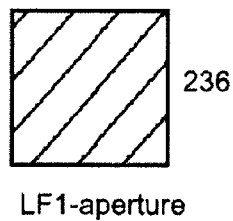
Figure 2D:
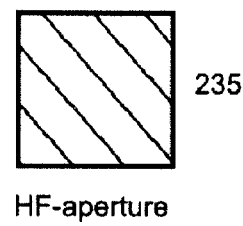

Hence, the invention provides solutions to different challenges for transmitting dual band pulse complexes, where a variety of radiation surfaces for the LF1 and HF pulses are selectable, as conceptually illustrated in FIG. 2d. The form of the apertures shown in FIG. 2d are circular for conceptual demonstration of the variations. However, the apertures may comprise any form such as, for example, rectangular, elliptical, or curved according to what a particular application requires. In FIG. 2d a first example of a radiation surface 230 illustrates a concept where an HF aperture 235 is common to parts of an LF1 aperture 236 in a common aperture 238. In this example, the LF1 aperture 235 also extends outside the HF aperture 236. A second example of a radiation surface 231 illustrates a modified concept where a central part 237 of the LF1 aperture 236 is inactive as LF1 radiation surface, for example to reduce the nonlinear interaction between the LF1 and HF pulses in the HF near field. A third example of a radiation surface 232 illustrates a concept where the inactive central part 237 of the LF1 aperture 236 is extended to be larger than the HF aperture 235. The fourth example of a radiation surface 233 shows a concept where the HF and LF1 apertures 235, 236 are equal. In many situations one wants to have an array where one can select between two or more of these conceptual situations for different operations of the measurement or imaging. The selection of the apertures can for example be done automatically by the instrument depending on the application, or manually by the instrument operator to optimize the image quality in a given measurement situation.

In yet another example application of a dual or multiple frequency band array according to the invention, different frequency bands are used to image at different depth ranges with the same probe, for optimized selection of frequency for different image depths. In this case, the HF band is used to image at lower depths for improved resolution with focus in these depths such as, for example, a switched linear array operating at 10 MHz, and the LF1 band is used to image at deeper depths with correspondingly deeper focus for improved penetration such as, for example, a linear phased array operating at 2.5 MHz. This type of probe is desirable with portable scanners, especially for emergency use, because the number of probes required to be carried around with the portable scanner is reduced. By dividing the apertures into array elements, the focal depths of both the LF1 and HF apertures and the beam directions can be electronically steered according to known methods. Due to the larger wavelength of the LF1 band, the array elements for the LF1 band may have larger radiation surfaces with larger distances between neighboring element centers than do the HF array elements within the common radiation surface (discussed in more detail below with respect to FIG. 5). In FIG. 2b the LF1 array 220 is composed of a single element, whereas the HF array 222 has a large number of elements. In FIG. 2c we also see that the LF1 and HF elements have different shapes. The present invention thus presents a general solution for a combined LF1 and HF array with a common radiation surface, which allows the apertures, frequencies and foci to be electronically selectable for optimal measurements in different applications, either automatically by the instrument depending on the application, or manually by the instrument operator to optimize image quality.

Figure 3A:
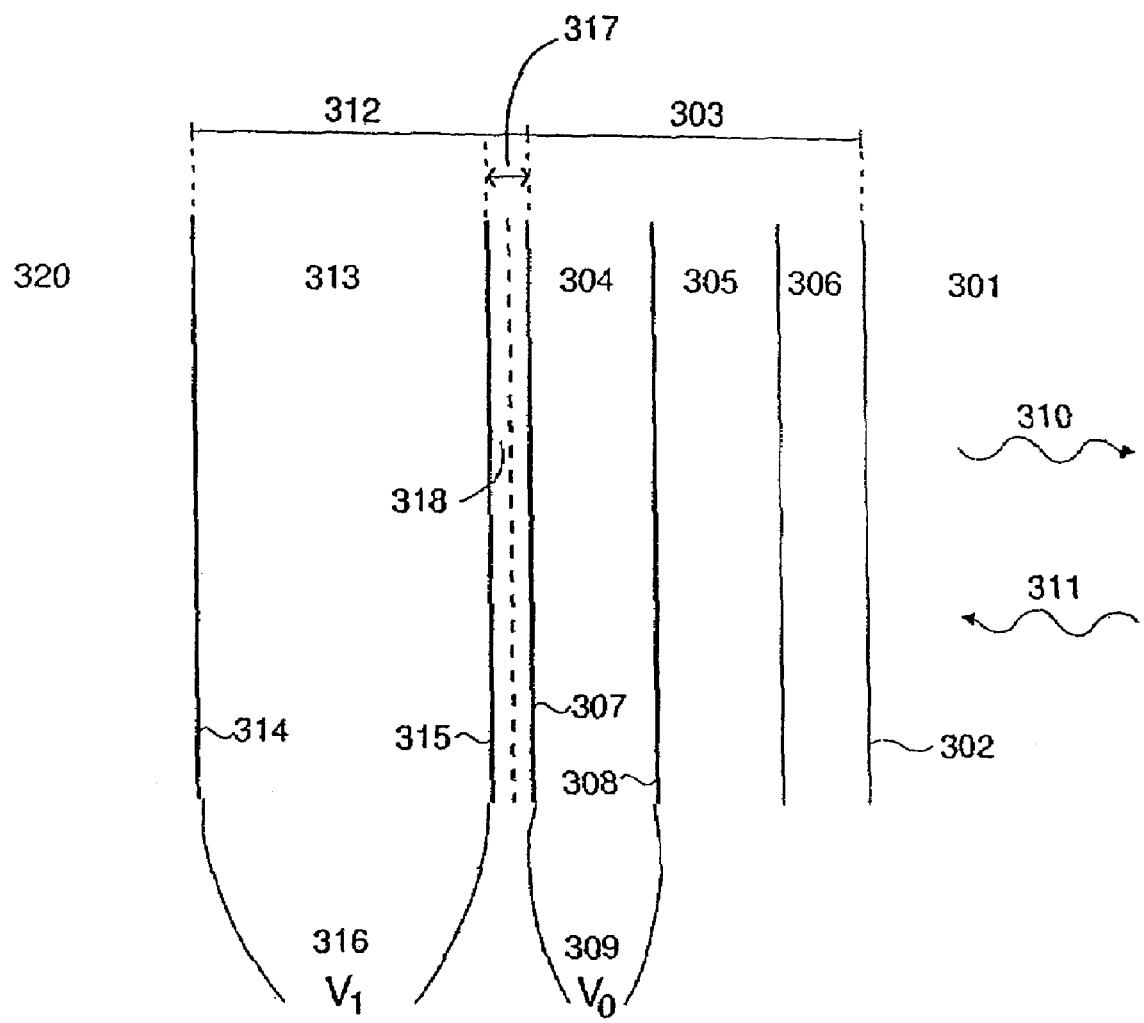
FIGS. 3a and 3e show cross sections of a dual and a triple piezo-layer stack arrangement embodiments according to the present invention that allows transmission and reception of a two and three frequency band pulses through a common front face, respectively.

The common radiation surfaces provide challenges in the structural design of electro/acoustic transduction due to the wide separation between the LF1 and HF frequency bands. The present invention provides several solutions to this problem. FIG. 3a shows a first example of a stack of piezoelectric and acoustic layers that allows operation of a LF1 and a HF pulse with widely separated frequencies from the same radiation surface. FIG. 3a shows a cross section through a layered structure that radiates and receives both frequency bands through radiation surfaces that at least have a common region 302 in acoustic contact with a load material 301. For typical applications, both the LF1 and the HF components might in addition be transmitted or received across separate surfaces outside the common surface. However, for equal LF1 and HF transfer functions across the whole aperture, it is advantageous to use the same thickness stack across the whole aperture, and define the LF1 and HF apertures by the areas of the active element electrodes as discussed below.

The HF pulse is received and/or generated by the transducer array assembly 303 which in this embodiment is composed of an HF piezoelectric layer 304 that is resonant in the HF band, with two acoustic matching layers 305 and 306 in front that acoustically connect to the load material 301. The acoustic contact can either be direct or through a fluid and a dome, all according to known methods. The HF piezoelectric layer 304 has a set of electrodes 307 and 308 on the front and back faces that electrically define the array elements. FIG. 3a shows the cross section of the electrodes 307 and 308 for one array element that generates the electric port 309 for that element. Driving the electric port 309 with a voltage signal $V_0$ in the HF band, will generate vibrations on the common region 302 of the radiating surface that generate a generated wave 310 propagating into the load material with frequencies in the high band. Similarly, an incoming wave 311 with frequencies in the high band will produce electrical voltage oscillations across the HF port 309.

The LF1 pulse is in this embodiment generated by the transducer array assembly 312, which is composed of an LF1 piezoelectric layer 313 that is resonant in the LF1 band, covered on the front with a layered isolation section 317 for acoustic isolation of HF vibrations in the HF structure from the LF1 structure. The isolation section 317 is designed so that the reflection coefficient between the HF assembly 303 towards the isolation section 317 is close to unity in the HF band to avoid interference from the LF1 structure on vibrations of the HF structure in the HF band. The isolation section 317 is also designed so that in the LF1 band it cooperates with the probe layers in front of the isolation section to provide acoustic matching of the LF1 piezoelectric layer 313 to the load material. When the LF1 piezo-layer is made as a ceramic/polymer composite it is advantageous that the isolation section 317 is made of at least two layers, where the back layer, or back group of layers, 318 of this section preferably is a heavy, impedance regularizing structure for reasons which will be described in more detail below. The whole transducer assembly is mounted on a backing material 320 with so high an absorption that reflected waves in the backing material can be neglected. In some embodiments impedance matching layers may be arranged between the LF1 piezoelectric layer 313 and the backing 320 to increase the acoustic coupling, according to known methods. FIG. 3a also shows a cross section of the electrodes 314 and 315 for a particular LF1 array element, or parts of the LF1 array element as the LF1 array element often is wider than the HF array element. The electrodes 314 and 315 constitute a LF1 electric port 316, where driving this port with an electric voltage signal $V_1$ in the LF1 band produces LF1 vibrations on the common region 302 of the radiating surface that radiates the generated wave 310 into the load material 301.

Close to unit reflection coefficient between the HF piezoelectric layer 304 and the isolation section 317 is obtained when the impedance seen into the isolation section 317 from the front is low or high compared to the characteristic impedance of the HF piezoelectric layer 304. When the impedance into the isolation section 317 from the front is low in the HF band, the HF piezoelectric layer 304 will have a thickness resonance when it is half a wavelength (or whole number of half wavelengths, where the half wave length is the most efficient) thick around the center of the HF band. When the impedance into the isolation section 317 from the front is high in the HF band, the HF piezoelectric layer 304 will have a thickness resonance when it is a quarter of a wavelength thick (or an odd number of quarter wavelengths) around the center of the HF band. The quarter wave resonance generally allows wider bandwidth of the HF layer resonance with poorer phase angle of the electrical impedance compared to for half wavelength resonance of the HF piezoelectric layer 304.

The thickness of the HF piezoelectric layer 304 is lower than the thickness of the LF1 piezoelectric layer 313 due to the separation of the HF and the LF1 frequencies. For this reason the cuts between elements or in the composite of the LF1 layer require a thicker saw blade than for the cuts in the HF layer. Thus, in the practical manufacturing situation it can be difficult to control whether the ceramic posts of the HF layer connect to ceramics or polymer fill in the LF1 piezoelectric layer 313. To make the HF isolation properties of the matching isolation section 317 have enough low sensitivity to a connection into LF1 ceramic or polymer fill, the back layer or group of layers 318 of the isolation section 317 that are adjacent to the LF1 piezoelectric layer 313 are made of heavy materials with high acoustic impedance such as, for example, metals like Ag, Cu, Au, Pd, Pt, and W, or even a ceramic material or integrated electronic substrates as discussed below. Large shear stiffness of the back layer(s) 318 will also help in reducing the sensitivity to connection of isolation section 317 into ceramic or polymer fill. However, a large shear stiffness of back layer(s) 318 would also introduce lateral vibration coupling between LF1 array elements. Thus, the thickness of the back layer(s) 318 should be limited, while still making the impedance seen from the front into the isolation section 317 adequately insensitive to connection into ceramic or polymer fill on the back side. Thicknesses of back layer(s) 318 less than λhd HF/20 are found useful, as discussed below. Of the listed metals, Ag, Au, Pd, and Pt have the lowest shear stiffness and still a high mass density which makes the materials most efficient for reducing the sensitivity to connection into ceramic or polymer fill with lowest lateral coupling between LF1 array elements.

The other layers of the isolation section 317 are typically chosen with $\lambda_{HF}/4$ thickness at the high frequency. A low impedance into the isolation section 317 may for example be obtained with a matching layer in front of the impedance regularizing back layer(s) 318, where the matching layer has low characteristic impedance and is quarter wavelength ($\lambda_{HF}/4$) thick at the center of the HF band. The matching layer is preferably made of polymer or similar material. A high impedance into the isolation section 317 can for example be obtained with a $1^{st}$ $\lambda_{HF}/4$ matching layer with low characteristic impedance to the front of the impedance regularizing back layer(s) 318 of large mass. This first matching layer connects into a second $\lambda_{HF}/4$ matching layer with high characteristic impedance that connects to the HF piezoelectric layer 304. The selection of characteristic impedances of the first and second matching layers can be done through standard considerations of impedance matching known to anyone skilled in the art. When the characteristic impedance of the $2^{nd}$ $\lambda_{HF}/4$ matching layer is adequately high, it is also possible to omit the impedance regularizing back layer(s) 318 without large modification of the HF electro-acoustic transfer function.

Figure 3B:
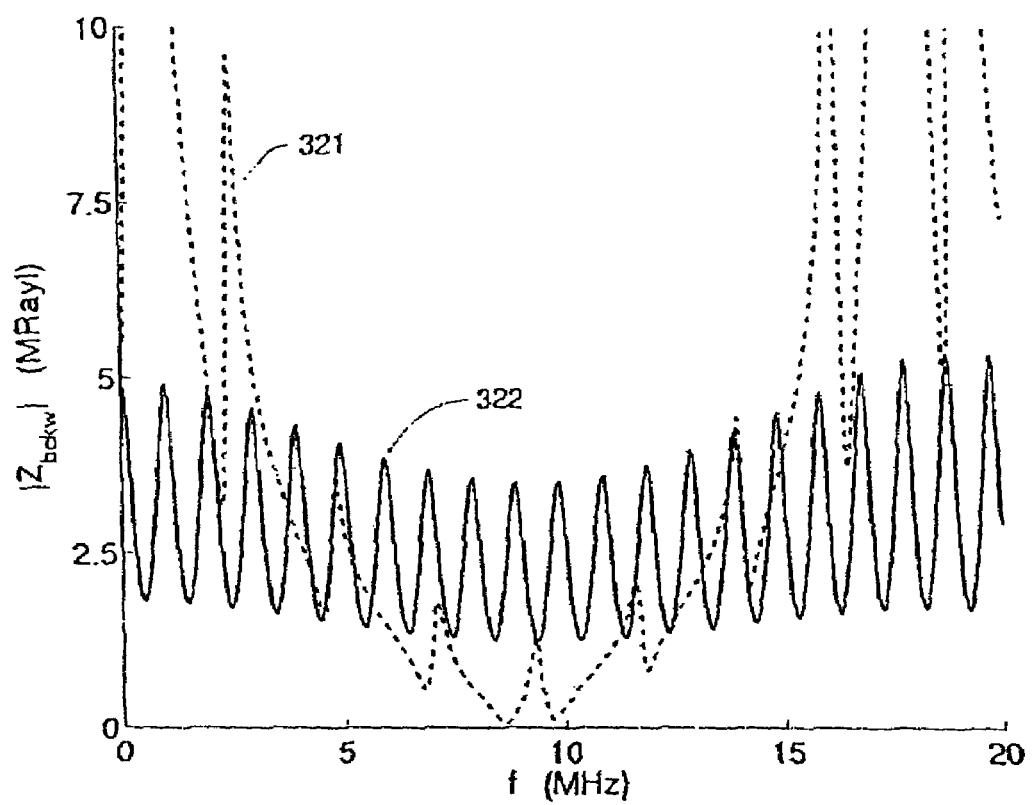
FIGS. 3b, 3c, and 3d show plots of impedance and frequency for various embodiments of the present invention.
Figure 3C:
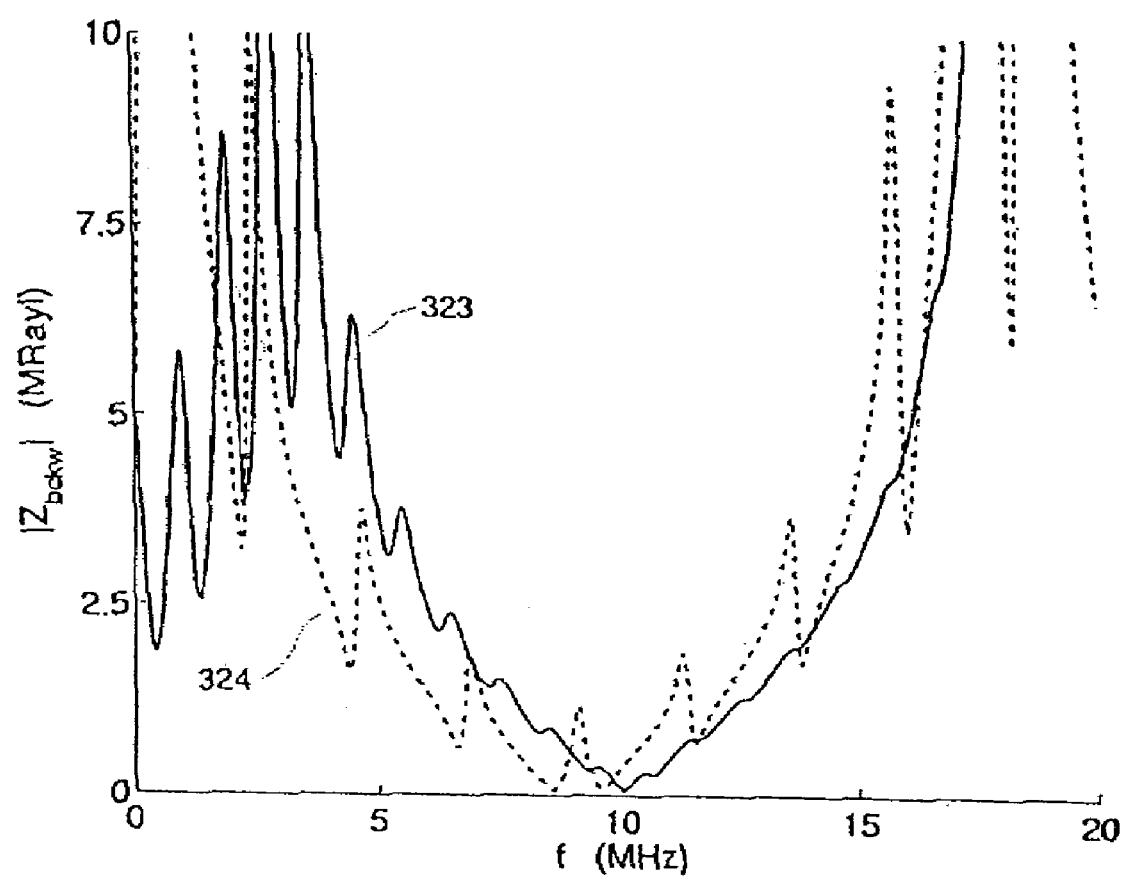
Figure 3D:
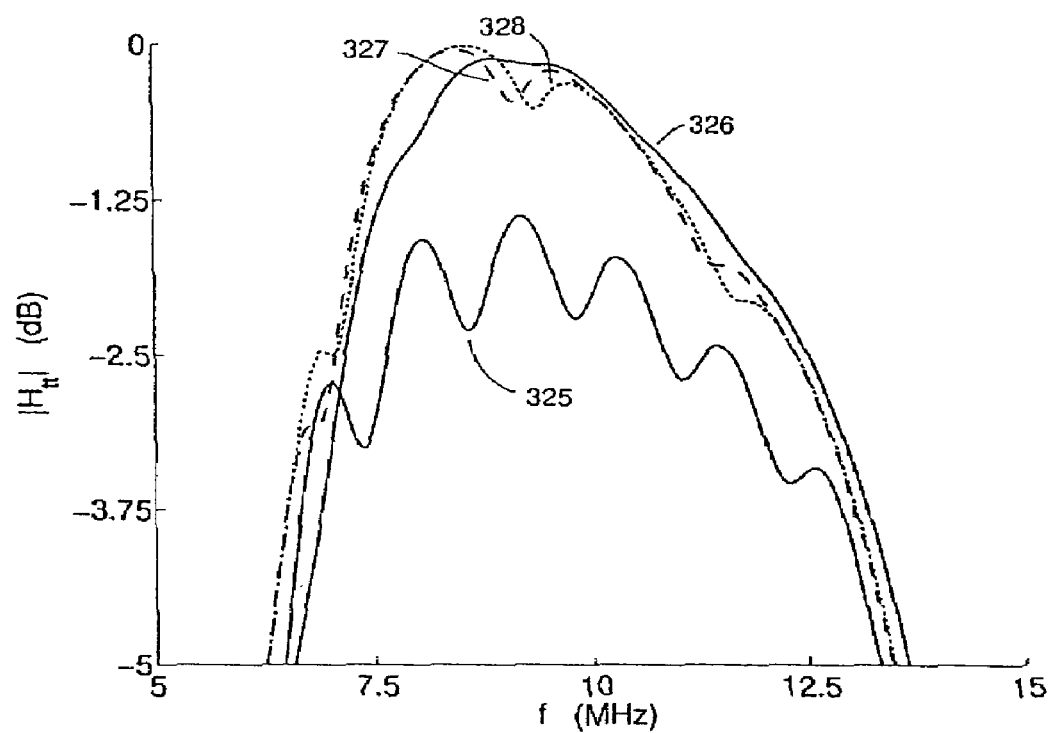
Figure 3D:
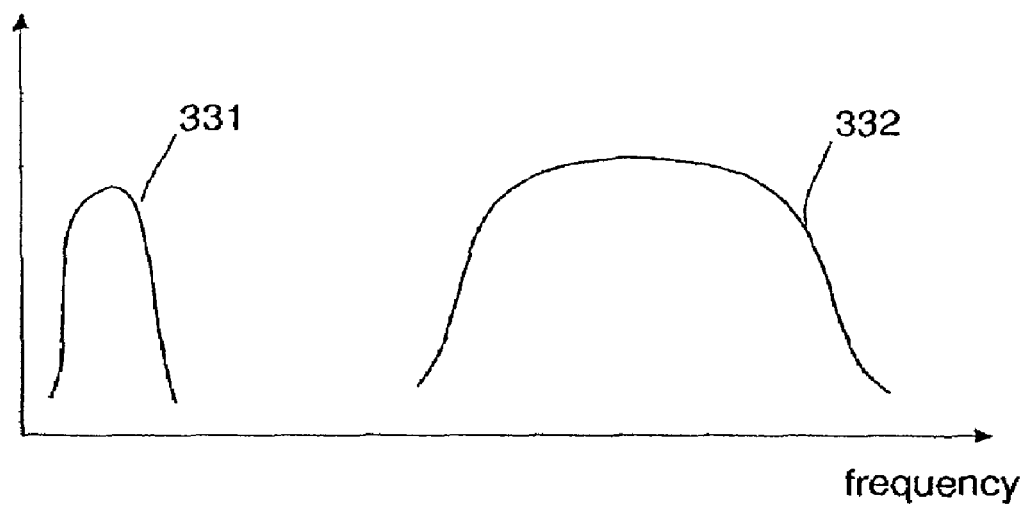

An example of the effect of back layers(s) 318 on the impedance seen into the section 317 from the front, is shown in FIG. 3b-d. In FIG. 3b the isolation section 317 is composed of a single polymer layer that is λ4 thick at 10 MHz. The curve 321 shows the acoustic impedance from the front into 317 as a function of frequency when the layer connects to the ceramic on the back. The impedance into the ceramics of LF1 piezoelectric layer 313 oscillates between a low value of the backing impedance $Z_B$ when the LF1 ceramic is a whole number of λ2 thick and a high value $(Z_{cer})^2/Z_B > Z_B$ when the LF1 ceramic is an odd number of □/4 thick. $Z_{cer}$ is the characteristic impedance of the ceramic. The $\lambda_{HF}/4$ polymer layer isolation section 317 then transforms this impedance into the curve 321 that oscillates with the frequency where close to 10 MHz we get a minimum value close to $(Z_{pol}/Z_{cer})^2 * Z_B$ and peak values close to $Z_{pol}^2/Z_B$, where $Z_{pol}$ is the characteristic impedance of the $\lambda_{HF}/4$ polymer layer. The curve 322 shows the impedance from the front into isolation section 317 as a function of frequency when the isolation section 317 connects to the polymer fill between the LF1 ceramic posts. The impedance into the polymer fill in LF1 piezolelectric layer 313 oscillates between a high value of the backing impedance $Z_B$ when the fill is a whole number of λ2 thick, and a low value $(Z_{fill})^2/Z_B < Z_B$ when the fill is an odd number of λ4 thick. $Z_{fill}$ is the characteristic impedance of the polymer fill between the ceramic posts in the ceramic/polymer composite of layer 313. The λ4 polymer layer isolation section 317 then transforms this impedance into an oscillating variation 322 where close to 10 MHz the peak values are close to $(Z_{pol}/Z_{fill})^2 * Z_B$ and minimum values are close to $Z_{pol}^2/Z_B$.

FIG. 3c shows the impedance seen from the front into isolation section 317 when a Cu back layer 318 of 20 μm thickness (about λ25 of Cu at 10 MHz) is introduced on the backside of the λhd HF/4 polymer layer of isolation section 317 described in FIG. 3b. The curve 323 shows the impedance seen from the front into the isolation section 317 when the Cu back layer 318 is connected to the polymer fill between the LF1 ceramic posts. The Cu back layer 318 of this thickness gives an added inductive impedance of the mass load of the Cu seen into the fill, which increases the impedance seen from the λhd HF/4 layer towards the back, and the $\lambda_{HF}/4$ layer inverts this impedance into an impedance <2 MRayl in the band 7-13 MHz which gives a very good isolation from the HF to the LF1 section in this band. The curve 324 shows the impedance seen into isolation section 317 when the isolation section 317 is connected to the LF1 ceramic posts. We note that the effect of the Cu back layer 318 makes less modification from the curve 321 to 324 than from the curve 322 to 323 when connecting to the polymer fill. The reason is that because the ceramic has a high characteristic impedance, the Cu back layer 318 mainly changes the frequencies of the low and the high impedance seen from the back of the λhd HF/4 layer, and not so much the value of the low and the high impedance. However, by using a sufficiently high backing impedance, for example $Z_B=5$ MRayl in this example, the maximal impedance seen into the isolation section 317 when connected to ceramic is still below 2 MRayl in the 7-13 MHz band, which gives a high isolation seen from the HF section in this band.

The effect of the Cu back layer 318 on the HF electro-acoustic transfer function is shown in FIG. 3d. The curve 325 shows the HF transfer function when isolation section 317 is composed of a single λhd HF/4 polymer layer as in FIG. 3b and connected to the polymer fill on the back. We note that this curve shows resonances due to internal HF reflections in the LF1 transducer array assembly section 312 because the impedance curve 322 does not provide adequate reflection at the back of the HF piezoelectric layer 304. Introducing a back layer 318 of 20 μm Cu changes this transfer function to curve 326 where the resonances due to reflections in the LF1 section 312 have disappeared. The curve 328 shows the transfer function without the back layer(s) 318 and when the section 317 is directly connected to ceramics. The transfer function of curve 326 moves to 327 when the Cu back layer is introduced. We note that the Cu back layer 318 removes the resonances in curve 325 and makes the transfer function 326 for connection into polymer fill and 328 for connection into ceramic of the LF1 section close to equal. Thus, FIG. 3d demonstrates that introducing the Cu back layer 318 makes the HF electro-acoustic transfer function insensitive to whether the isolation section connects to polymer fill or ceramics in the LF1 piezoelectric layer 313. The dual band electro-acoustic transfer function can then typically take the form as in FIG. 3d where 331 shows the transfer function for the LF1 port and 332 shows the transfer function for the HF port.

We should note that the important effect of this thin Cu back layer 318 is its mass, i.e., ρ L where ρ is the layer mass density and L is the layer thickness, that introduces an inductive impedance. The back layer(s) 318 is therefore conveniently made of any heavy material, such as Cu, Ag, Au, Pd, Pt, W, and ceramics, or alloys of these materials powders of these materials or alloys cintered together or glued in a solvent. The heaviest materials allows the thinnest layers, and as stated above the materials Ag, Au, Pd, and Pt have the lowest shear stiffness for their mass density and therefore produces the least lateral coupling between the LF1 elements. The wave propagation velocity for Si is 8.44 mm/μsec and for Al it is 6.4 mm/μsec. This allows quite thick (L) layers while still $L << \lambda_{HF}$ so that the layer has the effect of a mass load. Accordingly, adequate masses ρL for both Si and Al layers are achievable, as described below.

Figure 4A:
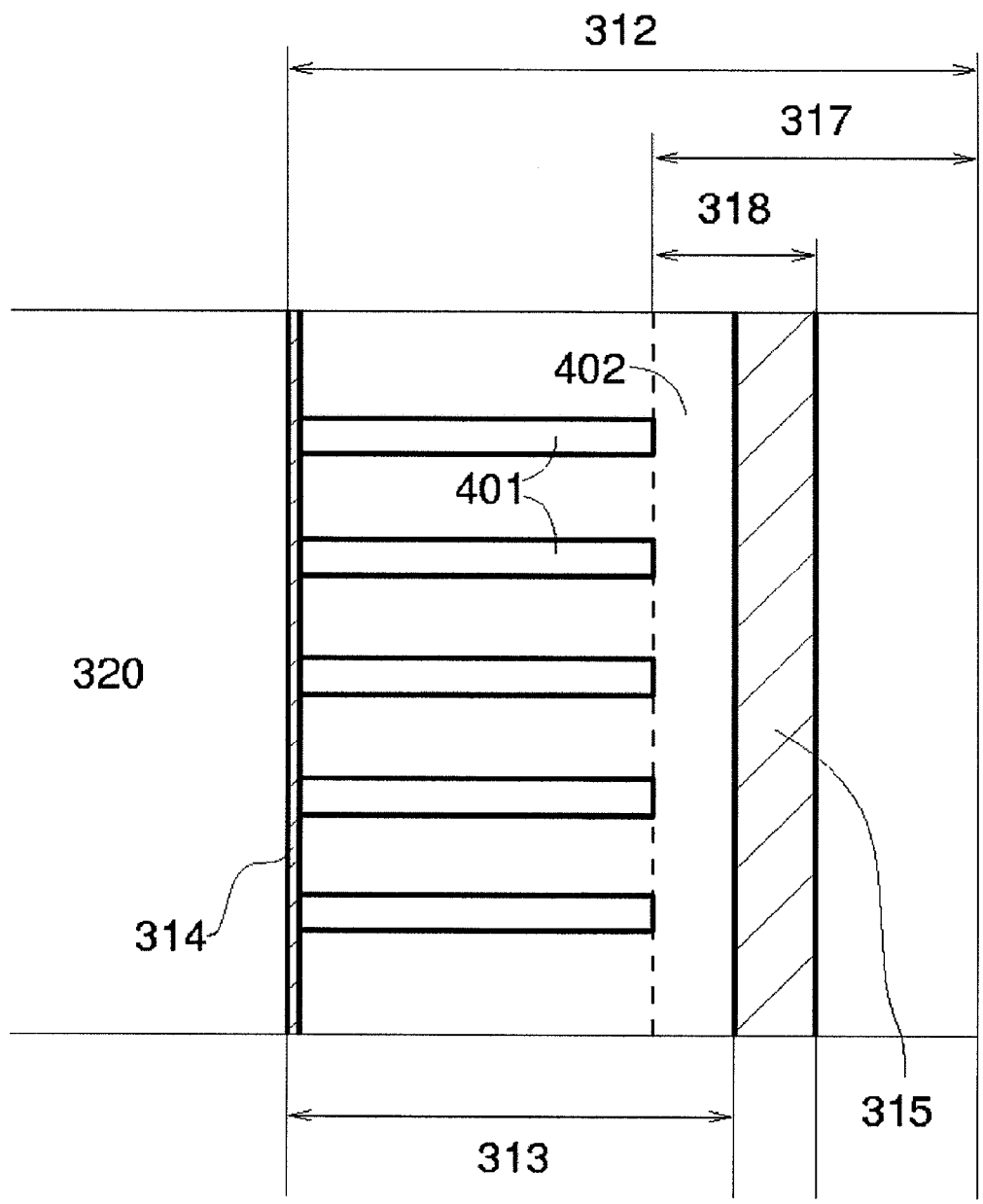
FIGS. 4a, 4b, and 4e show cross sections of other layer structures that participate in the isolation of the piezo-electric sections in FIG. 3, and also integrated circuit layers to be integrated in the acoustic stack.

The back layer(s) 318 may also include part of the ceramics in LF1 piezoelectric layer 313 as illustrated in FIG. 4a where the labeling for the same layers follows that in FIG. 3a. The polymer filled cuts 401 in the LF1 piezoelectric layer 313 are diced from the back of the layer but not diced completely through the LF1 piezoelectric layer 313 so that a complete ceramic layer 402 is left and included in the back layer(s) 318 of the isolation section 317. The LF1 front electrode 315 may also be made so thick that it has an acoustic effect in the HF band and also can be included as part of the back layer(s) 318.

An approximation for matching the LF1 piezoelectric layer 313 to the load in the LF1 band may be realized by assuming that both the matching layers of the isolation section 317 and the HF piezoelectric layer 304 with load matching layers will be thin compared to the wavelength in the LF1 band. A thin low impedance layer between high impedance layers will then approximately behave as an elastic spring in series with the rest of the structure, while the thin high impedance layers will behave as a series mass. When the isolation section 317 is composed of a single $\lambda_{HF}/4$ low impedance matching layer in front of the impedance regularizing back layer 318, for low impedance into the isolation section in the HF band, the LF1 piezoelectric layer 313 will to the front observe the elastic spring of the low impedance $\lambda_{HF}/4$ layer in series with the mass of the HF section 303 that is dominated by the mass of the HF piezoelectric layer 304. When the isolation section 317 has a second $\lambda_{HF}/4$ high impedance matching layer to obtain a high impedance into the isolation section as described above, this high impedance $\lambda_{HF}/4$ matching layer will give an added mass in series with the spring of the low impedance $\lambda_{HF}/4$ matching layer. The center frequency of the LF1 band may preferably then be selected around the resonance between this spring and mass system where the phase of the impedance into the matching layer of the isolation section 317 seen from the back is zero. This resonance frequency can be tuned by varying the stiffness of said low impedance $\lambda_{HF}/4$ matching layer and the mass density of the HF piezoelectric layer 304 and load matching layers (and high impedance $\lambda_{HF}/4$ matching layer of isolation section 317). This mass density can for example be tuned by varying the ceramic volume fill in the HF piezo-composite.

In a less efficient design to provide high impedance into the isolation section 317 in the HF band, a single $\lambda_{HF}/4$ matching layer with high characteristic impedance to the front of the impedance regularizing back layer 318 of large mass may be used. In the LF1 band this single matching layer will approximately behave as a mass in series with the mass of HF piezoelectric layer 304 and load matching layers and provide a load impedance seen from the LF1 piezoelectric layer 313 that has an inductive phase. This matching system does not provide optimal LF1 impedance resonant matching, but a useful form of the LF1 electro-acoustic transfer function is obtained.

Figure 3E:
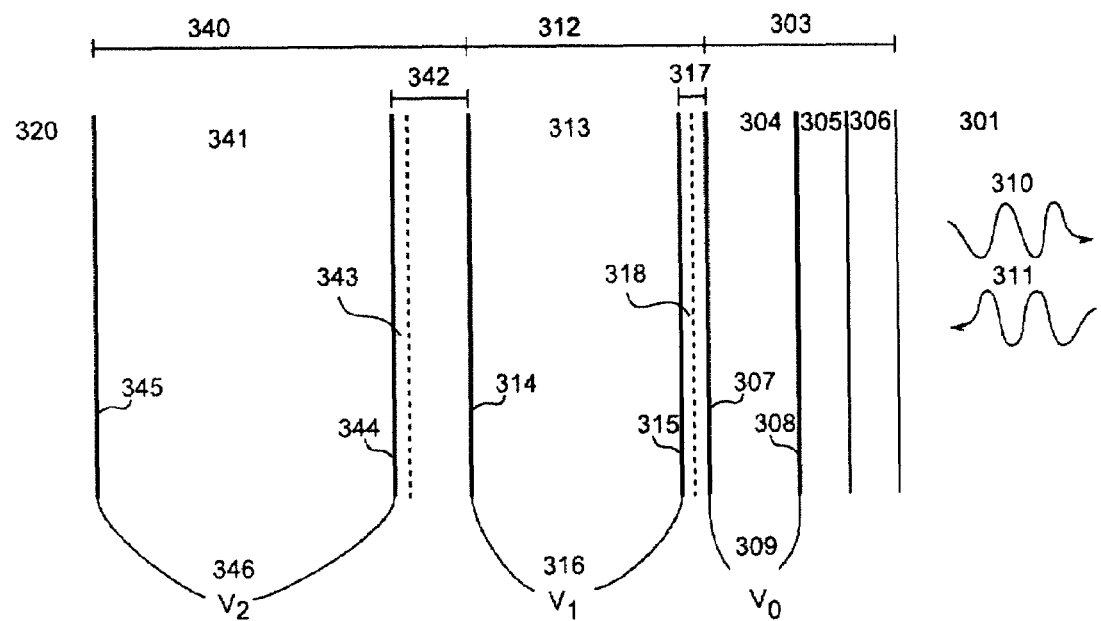
Figure 3E:
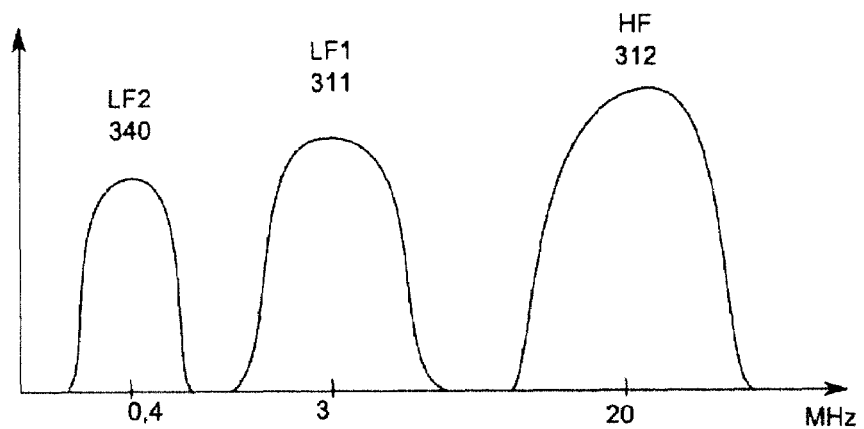

Using the method of an isolation section between piezoelectric layers, one can add piezoelectric layers at lower resonance frequencies backwards, in principle ad infinitum, for most applications with one or two layers. FIG. 3e illustrates the general principle by adding one more lower frequency layer to the structure in FIG. 3a. In FIG. 3e a second lower frequency section 340, referred to as LF2 is added to the back of the first lower frequency section 312, referred to as LF1. The layers of the LF1 and the HF sections 312 and 303 are given the same labeling as in FIG. 3a. The LF2 section 340 includes a piezoelectric layer 341 with an isolation section 342 to the front. The purpose of the isolation section 342 is to isolate vibrations in the LF1 band in the section 312 in front to propagate backwards into the LF2 section 340, to suppress the interference of LF2 section 340 with vibrations in the LF1 band in LF1 section 312, in the same manner as discussed for the HF isolation section 317 above. The front and back of the piezoelectric layer 341 are covered with electrodes 344 and 345 to form the electric port 346 of an element of the LF2 array. As stated above, the LF2 and LF1 arrays may comprise single element arrays. Alternatively, LF2 and LF1 may comprise multiple element, in which case FIG. 3e shows one of these array elements.

Isolation is obtained when the impedance into the isolation section 317, 342 from the front is either much higher than or much lower than the characteristic impedance of the neighboring piezo-layer 313, 341 in front. For a high impedance into 342 from the front, the piezo-layer 313 would operate at $\lambda_{LF}/4$ resonance, while with a low impedance into 342 from the front, the piezo-layer 313 would operate at $\lambda_{LF}/2$ resonance. The $\lambda_{LF}/2$ can be preferred at high medical ultrasound frequencies (~10 MHz and upwards) as this gives thicker piezo-layers that simplifies machining. For lower medical and SONAR frequencies, the $\lambda_{LF}/4$ resonance is preferred, as this gives wider bandwidth and requires less piezoceramic material that is expensive. If the piezoelectric layer 341 is made as a composite, the isolation section 342 is composed of at least two layers, where a back layer 343 is a heavy, impedance regularizing layer thinner than the LF1 wave length, similar to back layer 318, to reduce the difference in impedance when the ceramic posts of the LF1 piezoelectric layer 313 connects to ceramic posts or polymer fill in the LF2 piezoelectric layer 341.

In the LF2 band the layers in front of the LF2 section 340 are so thin that they function approximately as a spring or mass in series. The low impedance layers of the isolation section 342 then generally function as a spring in series with the mass of the layers in front, and the center of the LF2 band is selected at the resonance of this system as discussed for the LF1 band above. The backing material 320 may be used as an acoustic power absorbant to reduce peaking resonances in the electro-acoustic transfer functions. For improved acoustic coupling to the backing, acoustic matching layers may be introduced between the LF2 section 340 and the backing 320 according to known methods. Resonances in any of the frequency bands can also be dampened with matching layers of absorbing materials, for example viscous polymer materials, and even adding particles to the polymer materials to increase absorption. Viscous polymer materials and particle filled polymer materials can also be used in the polymer fills of the ceramic/polymer composites of the piezoelectric layers. Solid/polymer composites can also be used for matching layers to tune the characteristic impedance, where viscous and/or particle filled polymers can be used for increased absorption in the matching layers.

It is clear to those skilled in the art that the above procedure could be repeated by adding further lower frequency sections to the back, each section including its own piezoelectric layer for acousto-electric coupling and an isolation section for vibrations in the band of the neighbor section to the front. The procedure can thus be repeated in principle ad infinitum. However, most applications will require only a single or a dual lower frequency band.

FIG. 3a, e, and FIG. 4a show thickness structures for example elements or parts of elements of the arrays according to particular embodiments the present invention. However, one skilled in the art will appreciate that the present invention may be used to build acoustic arrays of various different organizations such as, for example, annular arrays, linear phased, linear switched arrays, or linear arrays with divisions in the elevation direction of many scales from 1.5D via 1.75D up to 2D arrays for full 3D steering of the beams. The lateral width (radiation surface) of an array element is typically limited by a ratio to the wavelength in the object. As the LF1 wavelength is larger than the HF wavelength, a wider LF1 array elements (larger element radiation surface) than HF array elements would be used. The isolation section in FIG. 3a and FIG. 4a then allows independent selection of the LF1 and HF array elements, as the HF isolation is practically independent of whether the isolation section terminates into ceramics or polymer. This for example also allows that the arrays for the different bands are of different nature, for example, but not limited to, a 1.5D linear switched array for the HF band and a linear phased array for the LF1 band. When the LF2 array is used for therapy, the beam direction does not have to be steered in some applications and the LF2 array may be made as a single element with fixed focus, or annular elements to steer the depth of the focus. With a single LF2 element composed of whole ceramic, the heavy back layer 343 of the isolation section 342 in front of the LF2 section 340 can be omitted, as the ceramic posts to the front would end in ceramics regardless of their lateral position.

When a multiple frequency probe according to the present invention is used for imaging at multiple depth ranges at different frequencies, the front HF array 303 may be a switched linear (or curvilinear) array, while the LF1 array 312 is used for phased array imaging. The required element pitch of the HF and the LF1 arrays can then be the same, for example 0.3 mm for a 7 MHz switched HF array, where the same pitch is $\lambda_{LF}/2$ for a phased array at 2.5 MHz. The structures of the isolation section 317 given above is however still useful as one would like to have more dense cuts in the HF ceramic/polymer composite than the LF1 composite, and the isolation section 317 as described above also allows less accurate lateral positioning between the HF and lower frequency arrays. The larger LF1 wavelength also favors the use of larger LF1 than HF transmit apertures as discussed above. For large depths, the HF receive aperture can however be larger than the LF1 transmit aperture, where in general one would favor a design with the same thickness structure throughout the whole array, and the size of the transmit and receive apertures can be varied by electrically selecting the elements that participate in the apertures (radiation surfaces). Which of the arrays (HF, LF1, LF2, . . . ) that is connected to the instrument beam former can be selected through electronic switches, but also through electric filters that would guide the different frequency transmit pulses to the array for the frequency, and similarly to guide the receive signals from the actual frequency band array to the beam former, all according to known methods. The arrays of any frequency band would show some sensitivity in the lower frequency bands, which can be suppressed by electrical filtering at the electric port. Sensitivity to the higher frequency bands is suppressed by the acoustic isolation sections 317, 342, so that one can omit the filter to the lowest frequency band.

Figure 4B:
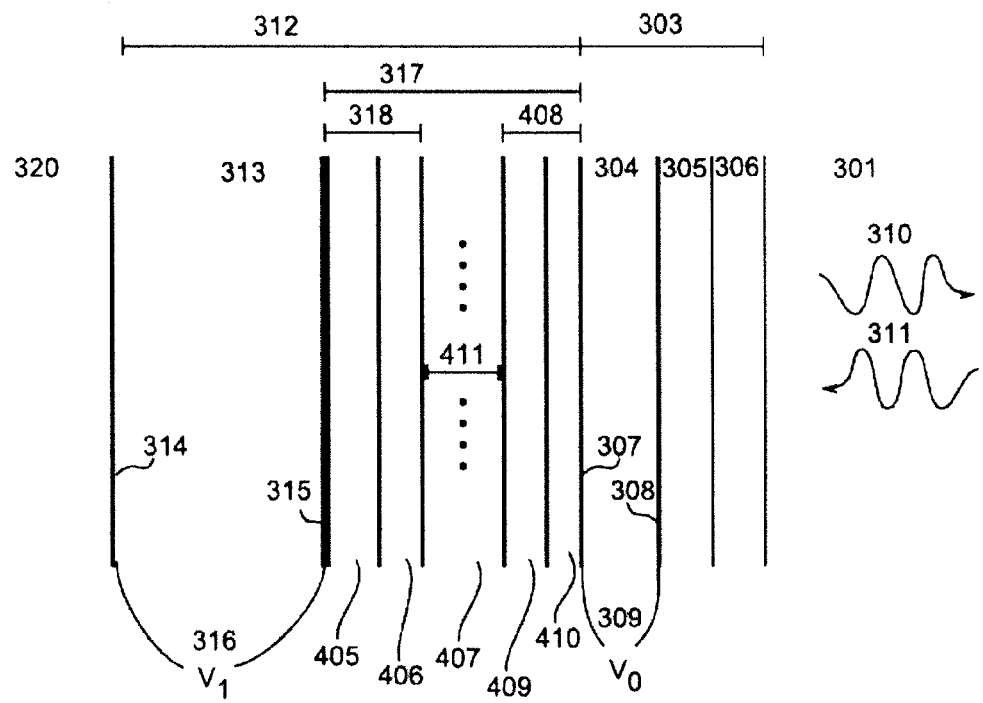
Figure 4B:
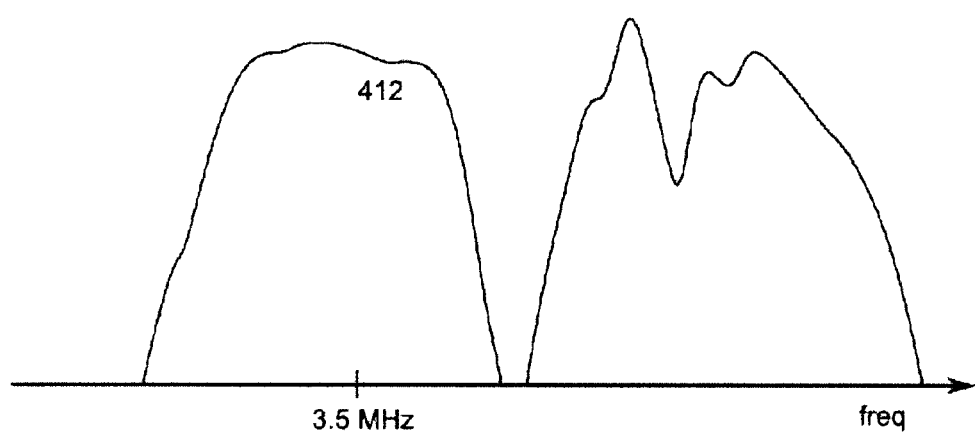
Figure 4C:
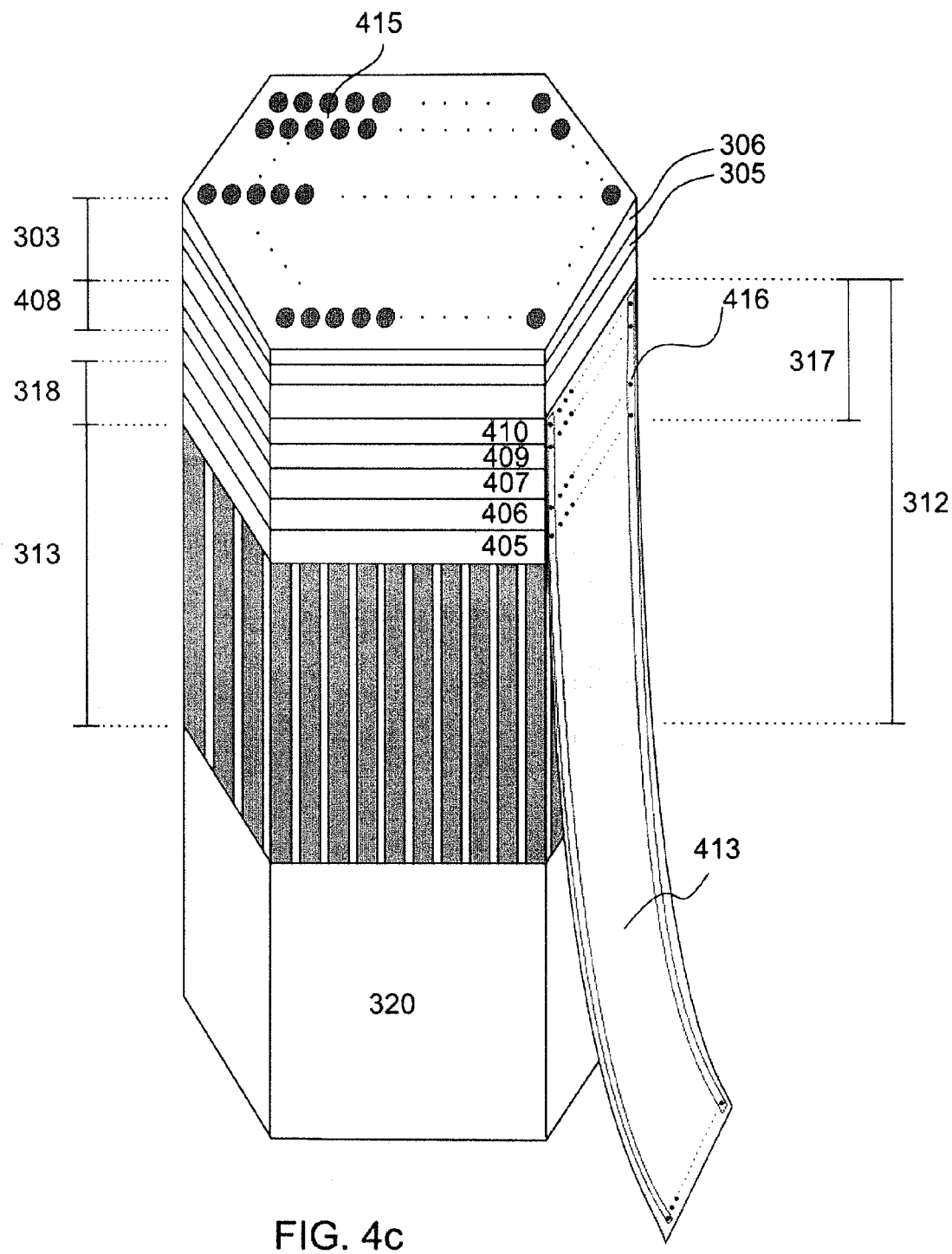
FIGS. 4c and 4d show perspective and top views of the embodiment of FIG. 4b.
Figure 4D:
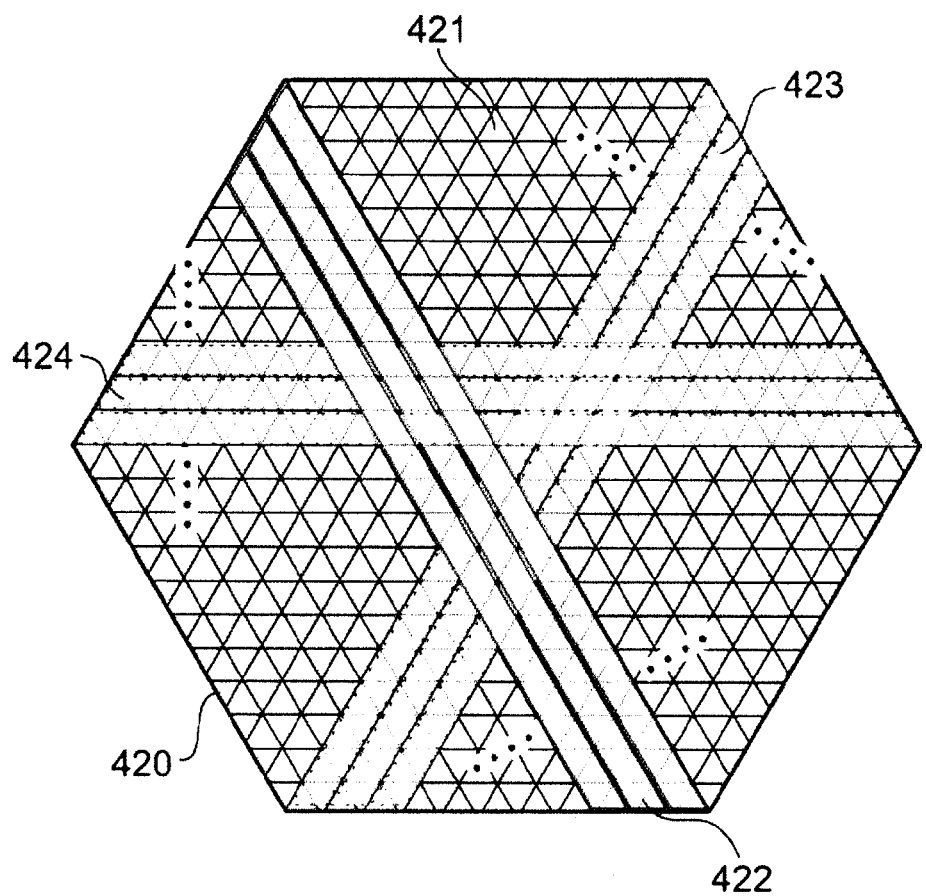
Figure 4D:
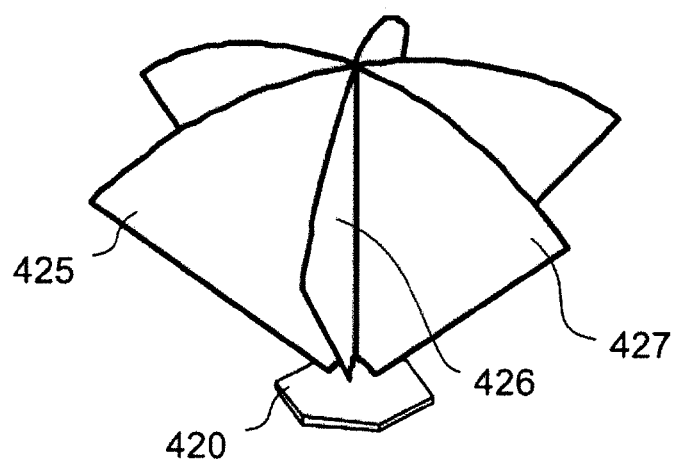

For the large number of elements that are found with some linear arrays but specially with 1.5D, 1.75D and full 2D arrays, the number of wires that connect the probe to the instrument may be reduced by including in the probe electronic circuits such as, for example, electronic switches that electronically selects and connects sub-groups of elements to the instrument beam former, or sub-aperture electronics that delay and combine the signal from several array elements into a single sub-aperture signal that connects to single channels in the instrument beam former, all according to known principles. The signals from groups of elements or groups of sub-apertures of elements may also be transmitted on a single cable by time-multiplexing samples of the signals from such groups, where the time-multiplexing circuits are integrated into the electronic substrate layers, to reduce the cable connections to the arrays. In general, the number of HF elements is greater than the number of LF1 elements, and thus more difficult to connect to electrically in the structure of FIGS. 3a and e. As will be described in detail below, electrical connection with electronic switches and/or sub-aperture electronics and/or time multiplexing for large element number HF arrays may conveniently be done with electronics on substrate layers as shown in FIG. 4b-d. For special high frequencies with less number of HF elements, the structures are also useful for amplifiers only, preferably receive amplifiers but in special situations also transmit amplifiers.

FIG. 4c discloses a 2D array concept probe according to the present invention including substrate layer, and operating at a HF frequency of 3.5 MHz and a LF1 frequency of 0.5 MHz. With a $\lambda_{HF}/2$ pitch of 0.22 mm, a 20 mm HF aperture with 90 HF elements 415 in a diameter results. With the hexagonal form of the aperture, a total number of HF elements 415 in the 2D array is approximately $90^2*3\text{root}(3)/8=5,261$ elements. Using sub-apertures of 5*5=25 elements, the total HF aperture is supported with 210 sub-apertures, which is a convenient number for cable connection to an instrument for final beam forming. The $\lambda_{LF}/2$ pitch for a LF1 frequency of 0.5 MHz is 1.54 mm, and one fills a 20 mm LF1 aperture diameter with 13 elements. For the hexagonal aperture the total number of LF1 elements in the 2D array is then approximately $13^2*3\text{root}(3)/8=110$ elements which is conveniently operated via a cable from an instrument with a LF1 transmit beam former in the instrument. For abdominal applications one could increase the diameter to 40 mm and the frequency to 5 MHz with $\lambda_{HF}/2$ pitch of 0.154 mm with a diameter of 256 elements and a total of $256^2*3\text{root}(3)/8=42,566$ elements. With 7*7=49 elements per sub-aperture we get in total 868 sub-apertures, and using a time multiplex factor of 7 per electric cable, we can connect to the HF array with 128 coax cables with 7× multiplex per cable. The LF1 array will then get a similar increase in number of elements.

In FIG. 4b substrate layers with integrated electronics are included in the HF isolation section 317, Si substrate layers are commonly used for integrated electronics and have a convenient characteristic impedance of 19.7 MRayl, which is a convenient value for a high impedance $\lambda_{HF}/4$ matching layer. Other substrate materials with high characteristic impedance, like GaAs, can also be used. In more detail, FIG. 4b shows the HF isolation section 317 with Si-substrate layers 405 and 406 included in the impedance regularizing back layer 318, a first low impedance $\lambda_{HF}/4$ layer 407, typically made of polymer, and a second high impedance $\lambda_{HF}/4$ layer 408 including two Si-substrate layers 409 and 410. The LF1 front electrode 315 may be made so thick that it gives acoustic contribution to the function of the back layer 318. The isolation function of the isolation section 317 is described above. Taking the example of the 2D 3.5/0.5 MHz array described above, we note that $\lambda_{Si}/4$ at 3.5 MHz is 0.6 mm, which gives 0.3 mm thickness of the two Si-substrates 409 and 410, which is a convenient thickness for integrated circuit electronics. One could even use lower thicknesses for more Si-layers or for higher frequencies. The thickness of each substrate could for example be reduced to 0.2 mm which would allow for 3 Si-substrate layers within the $\lambda_{HF}/4$ high impedance layer 408. At 10 MHz the $\lambda_{HF}/4$ length in Si is 0.211 mm that allows for a single Si substrate layer of this thickness in 408 at 10 MHz.

With 0.2 mm thickness of the Si-substrates 405 and 406, the back layer 318 will approach $\lambda_{HF}/4$ in thickness, which reduces the impedance regularizing effect of back layer 318, but with the structure of a first low impedance $\lambda_{HF}/4$ layer 407 and a second high impedance $\lambda_{HF}/4$ layer 408 one would still have a high impedance into the isolation section 317 from the front. The thickness of the back layer 318 could be reduced by reducing the amount of Si-substrate layers to one or even zero, depending on the amount of processing electronics to be arranged in the probe. The back layer 318 could alternatively be made thicker with more Si-substrate layers to allow for more processing electronics in the probe. The characteristic impedance of the LF1 ceramic/polymer layer 313 could be matched to the impedance of the back layer 318 so that they together define the resonance of the LF1 layer.

In one embodiment, the front substrate layer 410 contains receiver preamplifiers for the HF elements. The outputs of the preamplifiers may connect to the electronics in the second substrate layer 409 which includes sub-aperture beam forming electronics that delays and combines the signals from several HF elements into a single sub-aperture channel that considerably reduces the number of connections required to the instrument or further substrate layers of electronics. A reduced number of sub-aperture channels could then be transported to the instrument for final beam forming according to known methods. The final beam forming typically also includes corrections for wave front aberrations due to spatial variations in propagation velocity, according to known methods. In this case, the sub-aperture dimensions are limited by the correlation lengths of aberrations along the array surface.

The electronics in substrate layers 410 or 409 may additionally include switches that select subgroups of HF elements to the instrument beam former, for example as a switched array, or combining selected groups of 2D elements into linear elements of selectable direction as described in FIG. 4d. With the structure in FIG. 4b direct electrical connection between the HF array element electrodes and the front substrate layer 410 are obtained, where element electrodes connect to metal pads on the front substrate layer 410. Micro-soldering, ultrasonic bonding, anisotropic conducting polymer glue with conducting particles are all known and useful methods for the connection. With conducting polymer glue the max thickness of the glue must be limited to minimize wave reflection between the substrate layers. A polymer glue between the Si layers may be used to reduce the composite acoustic impedance of the substrate layers with glue. Electric connections between the stacked substrate layers are obtained through vias or through-holes in the substrates and/or with bonding at the edges of the layers, all according to known methods.

Electrical connections through an isolating layer 317, like the low impedance $\lambda_{HF}/4$ layer 407 may be realized using metallic connectors 411 through the layer, where said metallic connectors are so thin that they have minor effect on the characteristic acoustic impedance of said low impedance layer 407. In the example embodiment, the number of required connections through the isolating layer 407 can be greatly reduced by the circuits in substrate layers 409 and 410, which by the example array above is a reduction from 5261 to 210 connections through sub-aperture circuits. This illustrates the great advantage of channel reducing electronics in the high impedance section 408.

The HF acousto-electric transfer function is shown as 412 in FIG. 4b. The relative −3 dB bandwidth is ~70%, a high value that is partly achieved by the $\lambda_{HF}/4$ resonance of the HF piezoelectric layer 304 that is produced by the high impedance into the isolation section 317 in the HF band, produced by the high impedance λhd HF/4 matching back layer 408. At higher frequencies, a λhd HF/2 resonance of the HF piezoelectric layer 304 may be required to obtain a thicker layer that is easier to manufacture and handle. The resonance of the HF piezoelectric layer 304 can be considered to be a λhd HF/2 resonance of the composite HF piezoelectric layer 304 and the matching layer 408. Thus, the thickness of HF piezo-layer 304 may be increased at the expense of reducing the thickness of layer 408, for example by reducing the number of generating substrate layers, while maintaining the same center frequency of the HF band. With higher frequencies, a 1D, 1.25D, 1.5D or 1.75D switched array may be used instead a full 2D HF array, which all have less total number of elements. In that case, the HF elements may be connected directly through the isolating layer 407 to electronic layers in the back layer 318 via thin connectors as 411. In that case, the high impedance layer 408 may be omitted, which produces full $\lambda_{HF}/2$ resonance of the HF piezoelectric layer 304.

A schematic 3D rendering of the above-described probe with a 2D array according to the present invention, is illustrated in FIG. 4c, where the HF 2D elements are indicated as 415 on the front faces through the HF acoustic matching layers 305 and 306. The layers are given the same labeling as in FIG. 4b. Connection between the electronic substrate layers 405, 406, 409, 410 and the instrument may, for example, be obtained through connecting pads 416 at the edges of one or more of the substrate layers 405, 406, 409, 410. Flex print circuits 413 are conveniently connected to these pads 416 and arranged along side faces of the array structure and behind the backing where it can be connected to a flexible cable that connects to the instrument according to known methods. The connections between the substrate layers 405, 406, 409, 410 and the flex print circuits 413 can for example be obtained through micro-soldering, ultrasonic bonding, anisotropic conducting glue with conducting particles, or any other know or hereafter developed connecting methods. The flex print circuit 413 conveniently follows a flat side surface of the probe so that it adds only a minimal thickness to the probe.

Amplifiers, both transmit and receive, and sub-aperture circuits for the LF1 array can be placed in the substrate layers in front of the LF1 piezo-layer, typically behind potential substrate layers with electronics for the HF array (e.g., substrate layers 405, 406), and as part of the isolation group of layers 318. Depending on the space available, electronics for the LF1 and HF arrays could be placed on same substrate layers 405, 406. The substrate with LF1 electronics is typically located closest to the LF1 array. Substrate layers with electronics for the LF1 array can also be placed at the backside of the LF1 piezoelectric layer 313 in front of the backing material 320. With this last placements of the electronics, the connection to the cable connected to the instrument may be accomplished with wires through the backing material 320, where the wires are so thin that they do not propagate acoustic waves through the backing 320. The connection from the circuits to the cable may also be accomplished using the flex print circuit 413 on the side of the structure, as for the HF electronics described above. When placing the electronic substrates to the back of the array, the characteristic impedance of the piezoelectronic layer is preferably close to that of the substrate to minimize reflections between the substrate and the piezoelectronic layer so that the substrate layers participate in the definition of the LF1 resonance together with the LF1 piezoelectronic layer 313, as discussed for the front placement above. The net acoustic impedance of the substrate layers can also be reduced by thin intermediate layers of lower characteristic impedance, for example an anisotropic polymer glue as described above.

By connecting to the lowest frequency elements with wires through the backing 320, potential amplifiers, switching circuits, and sub-aperture circuits for the lowest frequency elements may be arranged behind of the backing 320 such as, for example, in stacked substrate layers with electronics, or with other arrangements according to known methods. Adequate space is typically available in the probe handle, so that this solution can be simpler than circuit layers stacked together with the LF1 array. The LF1 elements are however larger and fewer with lower frequency than the HF array, and the pay-off for connecting electronics in substrate layers to the LF1 section 312 is therefore less for using amplifiers and sub-aperture electronics in the probe itself for the HF section 303. As stated above, many embodiments according to the present invention will not require such circuits for the LF1 array in the probe.

Instead of using the sub-aperture method to form beams within a volume sector in front of the probe, a 2D array structure may use electronic switches in the electronic layers 409, 410 that connect groups of HF 2D elements into linear elements. Such an embodiment is shown in FIG. 4d, where the HF 2D array 420 is composed of triangular elements 421 that can be connected to sets of linear elements 422, 423, 424 that with phased array steering can be used to produce 2D scan planes in different directions illustrated as 425, 426, 427. With the 3.5/0.5 MHz example array above, it would then be sufficient with 96-128 channels in the HF phased array beam former. Selectable linear arrays with different directions of the linear elements could also be implemented with a dual piezoelectric layer structure as described in US Patent Application Publication US 2003/0216646.

Combination of 2D LF1 elements into linear LF1 elements could also for example be done in the electronic layers 405 and 406, or in electronics of other arrangements, or via a dual layer structure as described in US Patent Application Publication US 2003/0216646. For the LF1 linear array beam former in the example array above it would then be sufficient with 13 channels. However, the number of total LF1 array elements in the example array described above is only 110, so that one could also connect all LF1 elements to the instrument and do the LF1 element combination in the instrument. This would provide full flexibility in the use of the LF1 array as a 2D volume scanning array or as a linear array with selectable 2D scan directions. It would then be convenient that the electronics in layers 405-410 would also include both sub-aperture connection to the 2D HF array for full volume sector scanning of the HF beam together with such scanning of the LF1 beam, and connection of 2D elements into linear elements for 2D sector scanning of the HF beam together with the LF1 beam.

LF1 transmit beam former electronics in the probe is especially interesting when the LF1 array is used for transmit only, as described with the methods in U.S. Patent Application Publication No. 2005/0277835 and U.S. Patent Application Publication No. US 2006/0052699 A1, where only a transmit sub-aperture beam former is needed. For transmit amplifiers that switch the element signals to positive and negative power voltages, power losses can be made so low that the entire transmit beam former with amplifiers can be integrated into the probe. Such a probe would have a simplified connection to existing scanners, for direct field upgrade to existing scanners with the methods described in U.S. Patent Application Publication No. 2005/0277835 and U.S. Patent Application Publication No. US 2006/0052699 A1.

Figure 4E:
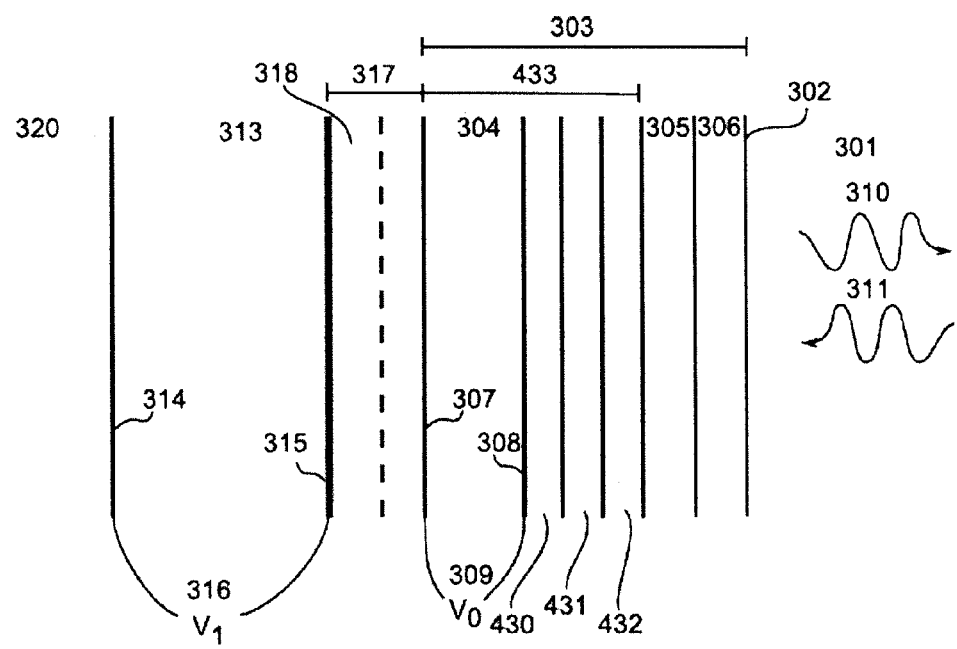

Making the HF piezoelectric layer 304 with close to the same characteristic impedance as the Si-substrates, one could also place Si-substrate layers 430, 431, 432 to the front of the HF piezoelectric layer 304 as illustrated in FIG. 4e. The HF resonance is then defined by the combined thickness of the piezo-layer 304 and the Si-substrate layers 430, 431, 432, i.e., the structure 433. A simulated electro-acoustic HF transfer function for this structure is shown as 434 in FIG. 4e.

The example placements of electronic substrates within the acoustic structure in FIG. 4b-e can also be combined and modified in various forms for simplified connection between the HF and LF1 array elements, the substrate electronics, and the instrument beam former. The probe could typically also contain electronic circuits in the handle, behind the backing material.

Figure 5:
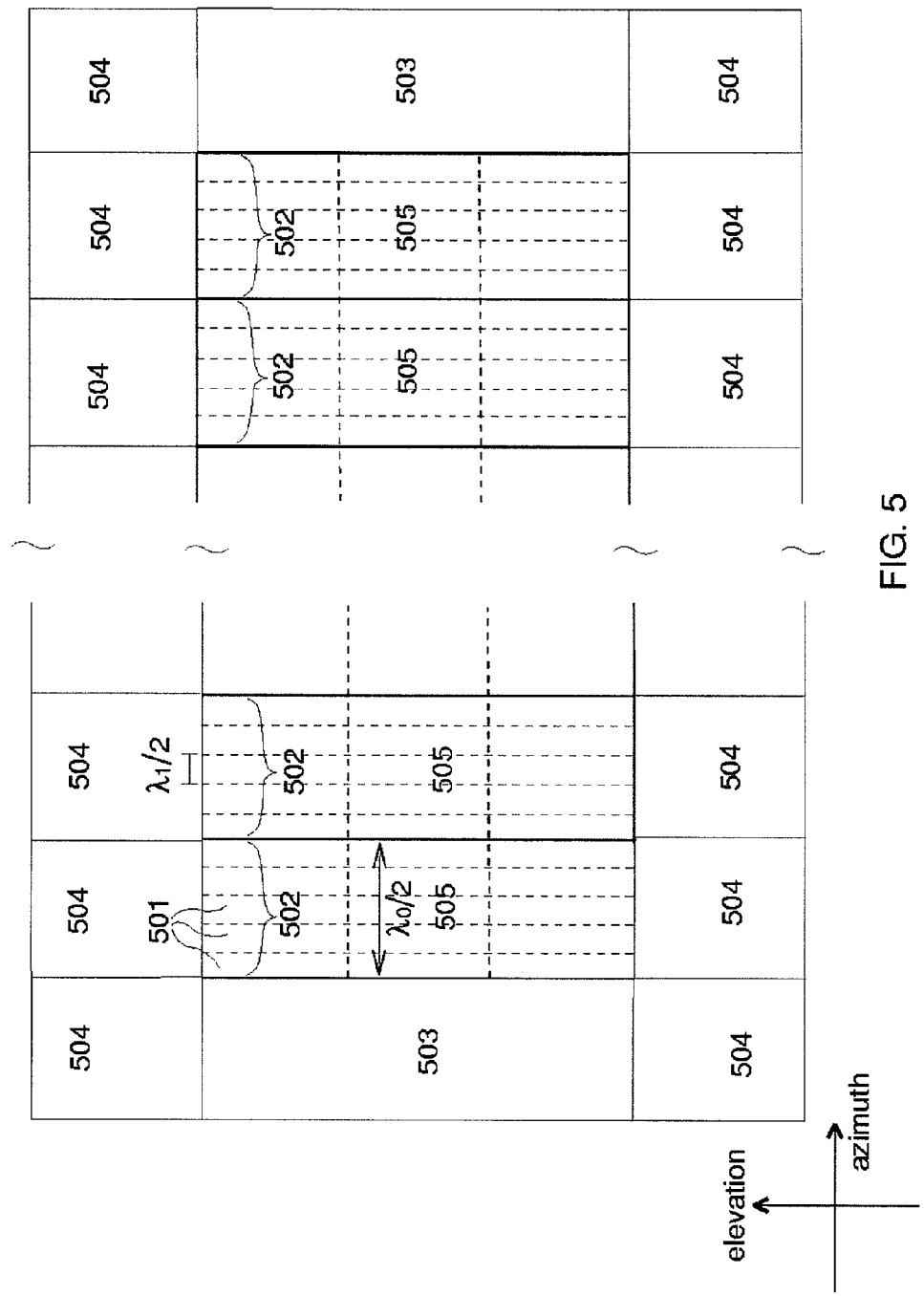
FIG. 5 is a front view of an embodiment of a phased array probe according to the present invention.

FIG. 5 is a front face view of another embodiment of a linear phased array according to the present invention. HF array elements 501 of a phased array HF aperture are shown, where $\lambda_1$ is the HF wave length and a pitch of the HF elements is $\lambda_1/2$. With proper steering of the signal on each of the HF array elements 501 according to known methods, such an array allows steering of the beam direction within a sector in the azimuth direction. Steering in the elevation direction requires division of the elements also in the elevation direction into a two-dimensional (2D) array, and we will at this point emphasize that the basic methods of the present invention are also applicable to 2D arrays.

The center of the HF band of this linear array is by example $f_1=3.5$ MHz which suggests a high frequency element pitch of $\lambda_1/2 \sim 0.22$ mm. 84 HF array elements 501 then produces a total aperture of 18.48 mm. If a center of the low frequency band of $f_0=0.5$ MHz, then $\lambda_0/2 \sim 1.54$ mm, which suggests 12 of the low frequency elements 502 that produces a total aperture of 18.48 mm. For better collimation of the LF1 beam, extra LF1 elements could be added to each side of the HF elements. FIG. 5 shows by way of example two such LF1 elements 503 increasing the LF1 azimuth aperture to 14 elements ~21.56 mm. To increase the LF1 elevation aperture one could similarly expand the LF1 aperture by the elements in the elevation direction, where the Figure shows by way of example the LF1 elements 504. As follows from the analysis in relation to FIG. 2a-d, the same transmit aperture of the LF1 and HF radiation surfaces is required in some application when it is critical that the phase between the HF and LF1 pulses has minimal sliding with depth. For other applications which require higher LF1 amplitude at large depths, it is desirable that the LF1 transmit aperture is larger than the HF transmit aperture to reduce diffraction broadening of the LF1 beam with depth. To reduce the nonlinear manipulation by the LF1 pulse in the propagation and scattering of the HF pulse close to the array, the central radiation surface of the LF1 array. This is accomplished by further dividing the LF1 elements into the LF1 sub-elements 505. The LF1 array in FIG. 5 then allows selection of the size of the LF1 aperture, for example as one of 1) equal to the HF aperture, 2) larger than the HF aperture either in the azimuth and elevation directions separately or in both the azimuth and elevation direction, and 3) having an inactive area in the center of the HF aperture. Such variation of the LF1 aperture relative to the HF aperture may be obtained with other array configurations such as, for example, 2D arrays and annular arrays, and those skilled in the art can apply the teachings of the present invention to all those array configurations. For many applications only the second configuration of the LF1 aperture is required in which the LF1 aperture is larger either in the azimuth and elevation directions separately or in both the azimuth and elevation direction. This configuration is achieved by combining the LF1 elements 502/504/505 into a single LF1 element with elevation dimension equal to or larger than the HF aperture, and adding extra LF1 elements 503/504 in the azimuth direction to obtain a LF1 aperture that is also larger than the HF aperture in the azimuth direction.

To obtain the same vibration conditions for the LF1 elements over their whole area, a stack such as the stack of layers shown in FIGS. 3 and 4 for the whole array area may be used, wherein the LF1 and HF elements are defined by the element electrodes 307, 308, 314, 315 and cuts in the piezoelectric layers 304, 313 as described above. It is also advantageous to use ceramic/polymer composites for both HF and LF1 piezoelectric layers 304, 313, where the element dimensions are defined by the electrodes. The HF radiation area could then, for example, be defined by a common ground electrode on the front side which defines the elevation width of the elements both through electrical coupling and also by defining the areas of the ferroelectric ceramic that is polarized to show piezoelectric properties. The azimuth width of the HF elements are then defined by the back side hot electrodes which can conveniently be extended to the edge of the assembly for electrical connection to the cable as the electro-acoustic coupling outside the ground electrode is low, both due to reduced electric field and reduced electric polarization of the ferroelectric ceramic material.

The isolation section 317 in FIGS. 3 and 4 makes accurate position matching between cuts in the HF and LF1 piezoelectric layers 304, 313 less critical, as the impedance seen into the section 317 from the front has little variation with termination into polymer or ceramic, as for example discussed in relation to FIG. 3b-d. This reduced sensitivity allows dicing of the piezoelectric layer 313 with thicker saw than the HF piezoelectric layer 304, and also reduces requirements for accurate lateral positioning between the HF and LF1 piezoelectric layers 304, 313.

The HF array in FIG. 5 could also be used as a switched linear array where the HF beams are normal to the HF aperture. In some applications, it is useful to make the LF1 array as a single element, that provides an unfocused LF1 aperture. In this case, the LF1 aperture is chosen to be sufficiently large so that the entire HF imaging depth is within the near field of the aperture, as described above. For suppression of multiple scattering noise, for example as described in U.S. Patent Application Publication No. 2005/0277835, the portion of the LF1 transmit aperture composed of the elements 502 and 505 could be removed. For flexibility, the aperture could then be composed of two elements: i) a central element including elements 502 and 505 connected in parallel, and ii) an outer element including the elements 504 and 503 connected in parallel. For nonlinear imaging one would use both the central and outer LF1 elements in parallel for the LF1 transmit aperture, while for suppression of multiple scattering noise one could take the central element from the LF1 transmit aperture.

It is also known that the piezoelectric layers 304, 313 and 341 may comprise multiple layers, both piezoelectric and non-piezoelectric, to alter and increase the bandwidth of the electro/acoustic transfer functions and reduce the electric impedance of the electric ports. Adding the stacks of substrate layer exemplified in FIGS. 4b and 4e can be considered a way to add a non-piezoelectric layer that interferes with the resonance definition, for example as described in U.S. Pat. No. 6,645,150. To obtain lower electric impedance of the array elements (especially the lower frequency elements) for the purpose of transmitting high pressures with manageable drive voltage amplitudes, one or more of the piezoelectric layers 304, 313 and 341 may comprise a stack including a plurality of piezoelectric layers covered with electrodes.

Figure 6:
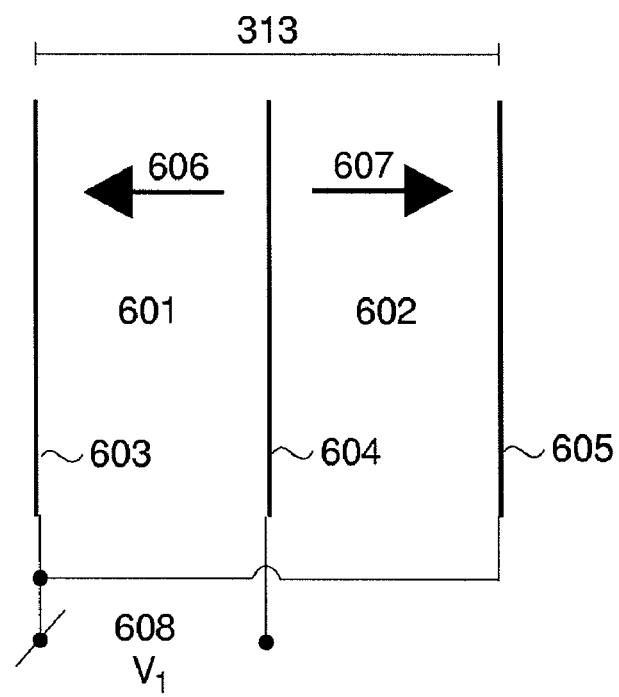
FIG. 6 shows an example of a dual piezolayer arrangement to reduce the electric impedance of array elements.

FIG. 6 shows an example embodiment of a piezoelectric layer 313 having two layers 601 and 602 which are covered with the electrodes 603, 604, and 605. Typically, one would galvanically connect electrodes 603 and 605 to ground where the electrode 604 would be used as the hot electrode. The two piezoelectric layers 601 and 602 would then have opposite polarization directions 606 and 607, so that the electrode coupling would provide an electrical parallel coupling of the layers 601 and 602 to provide a lower electric impedance port 608 Such a configuration allows driving the low frequency array with lower voltages for the high pressures. For improved bandwidth of the layers, a high impedance layer in front of the active piezoelectric layers may be introduced, as presented in U.S. Pat. No. 6,645,150. Parallel coupling of more than two layers may be done to achieve even lower electric port impedance. The above may also be implemented in the HF piezoelectric layer 304, according to known methods. US Patent Application Publication No. US 2003/0216646 describes how dual layers can by used obtain linear arrays with selectable direction of the electrodes, for electronic rotation of the 2D scan plane. This solution is interesting both for the higher and lower frequency arrays within the structure of the present invention.

Figure 7:
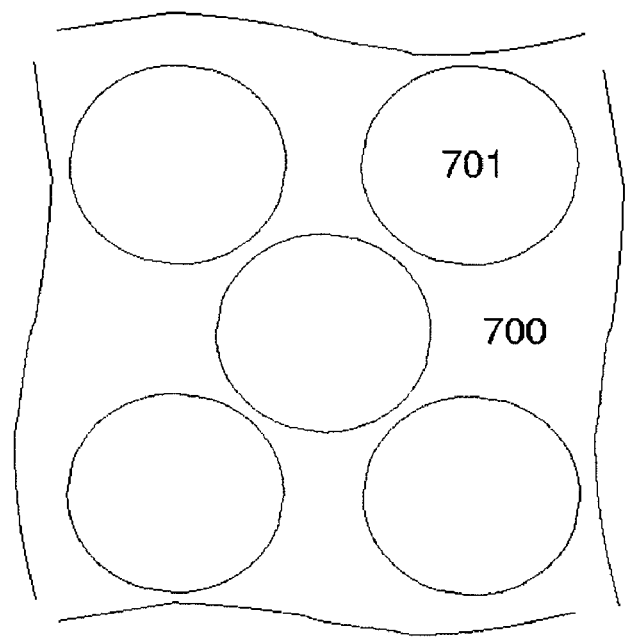
FIG. 7 is a front view of a substrate with cmut/pmut micro-machined transduction cells.

According to another embodiment, the electro-acoustic transduction is based on micro-machined transduction cells on the surface of a substrate such as, for example, a Si (silicon) substrate, or other substrate of materials such as Cu and Al. With these techniques, increased vibration of the surface is obtained by vibrating membranes on the substrate surface, with gas or vacuum behind the membrane, where the membrane connects to the acoustic load material either directly or through acoustic layers. The electromechanical coupling is obtained by capacitive coupling from the membrane to a reference electrode, referred to as cmuts (capacitive micromachined ultrasound transducers), or by piezoelectric films on the membranes, referred to as pmuts (piezolayer micromachined ultrasound transducers). FIG. 7 shows a front face of a substrate 700 with such membranes 701 arranged thereon. The dimensions and thicknesses of the membranes 701 determine the resonant band where the transduction is most efficient, and several of the cmut/pmut cells are usually coupled together electrically to form one array element. In the current invention we are concerned with inventive implementations of the cmut/pmut techniques to transmit dual or triple band pulses from essentially the same radiating surfaces. The Figures show inventive steps to achieve the dual or triple band function, and the details of the membranes, electrodes, and electrical connections are made according to known or hereafter developed solutions. We shall in the following refer to this technology as cmut/pmut transducers, cmut/pmut cells, and cmut/pmut drums or membranes.

Figure 8A:
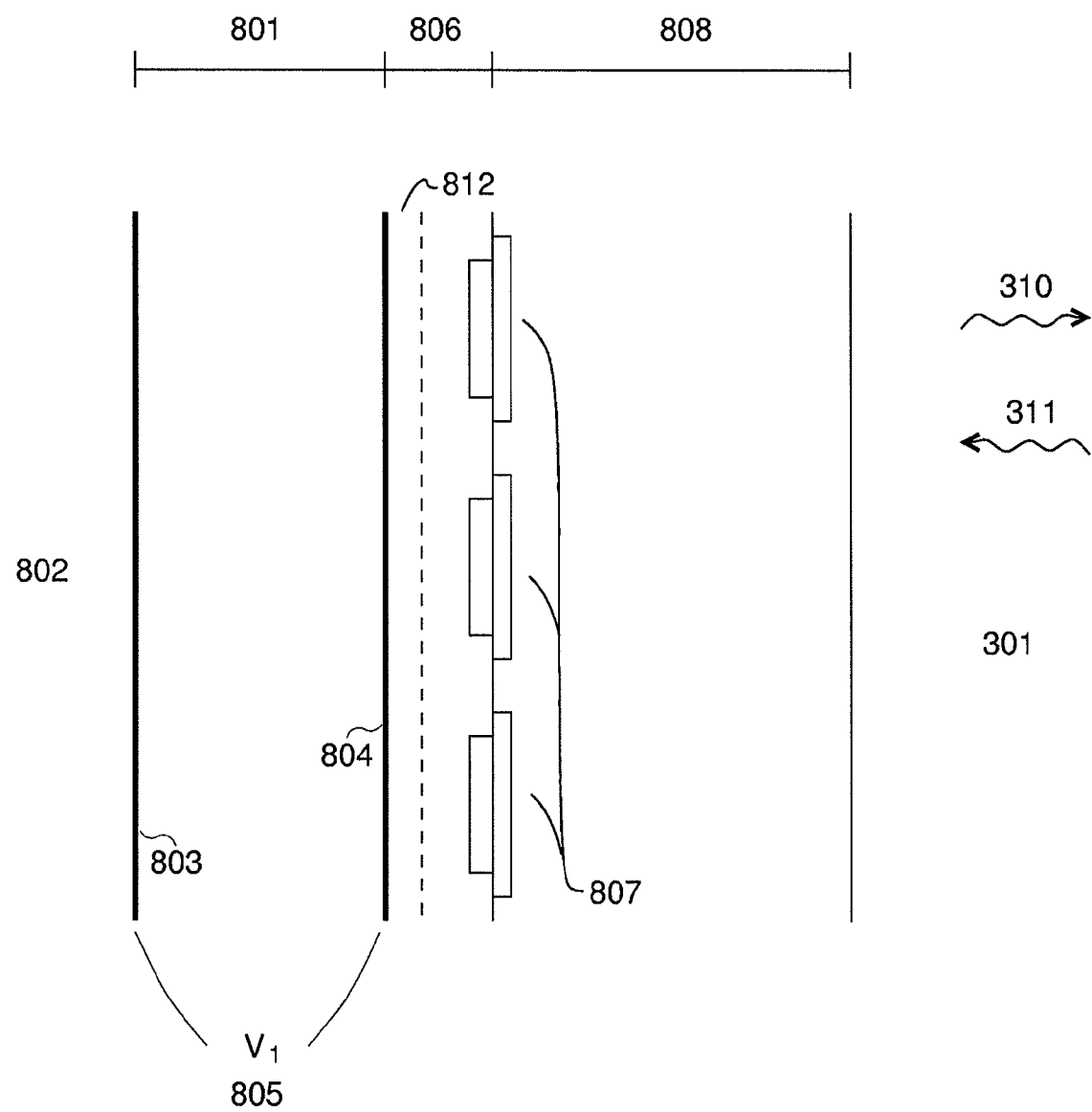
FIGS. 8a, 8b, and 8c show transducer stack embodiments of the present invention in which HF transduction is generated by cmut/pmut cells on a substrate in front of a piezolayer for LF1 transduction, and which also includes substrate layers with integrated electronics.

The characteristic impedance of Si is 19.7 MRayl and Al is 17.4 Mrayl, which characteristics may be exploited as described below for transmitting the LF1 wave through an HF substrate. FIG. 8a shows a cross section of a structure with a cmut/pmut HF section 806 with cmut/pmut drums 807 mounted in front of an LF1 section including a piezoelectric layer 801 with electrodes 803 and 804 generating the LF1 element electric port 805. Details of the cmut/pmut drums 807 and associated electrodes and electrical coupling are not shown and are made according to knows or hereafter developed solutions. The total structure in this embodiment is mounted on a backing material 802 (which can be low impedance or air). A protection structure 808 is placed in front of the cmut/pmut drums 807. The protection structure 808 includes one or more layers designed for acoustic impedance matching between the load 301 and the cmut/pmut HF section 806, and absorption layers to reduce lateral coupling between array elements along the substrate. The protection structure 808 optionally contain an acoustic lens that focuses the acoustic beams.

FIG. 8a also shows an optional absorbing layer 812 to reduce lateral acoustic coupling in the Si or Al substrate between the HF array elements (i.e., cmut/pmut drums 807) and also between the substrate and the LF1 section in the HF frequency band. The cmut/pmut drums 807 reduce the effective acoustic impedance of the HF section 806 below that of Si/Al. By making the piezoelectric layer 801 as a ceramic/polymer composite, the acoustic impedances of layer 801 and 806/808 can be matched so that the reflection coefficient between the piezoelectric layer 801 and the HF section 806 is low for improved bandwidth of the LF1 port.

Figure 8B:
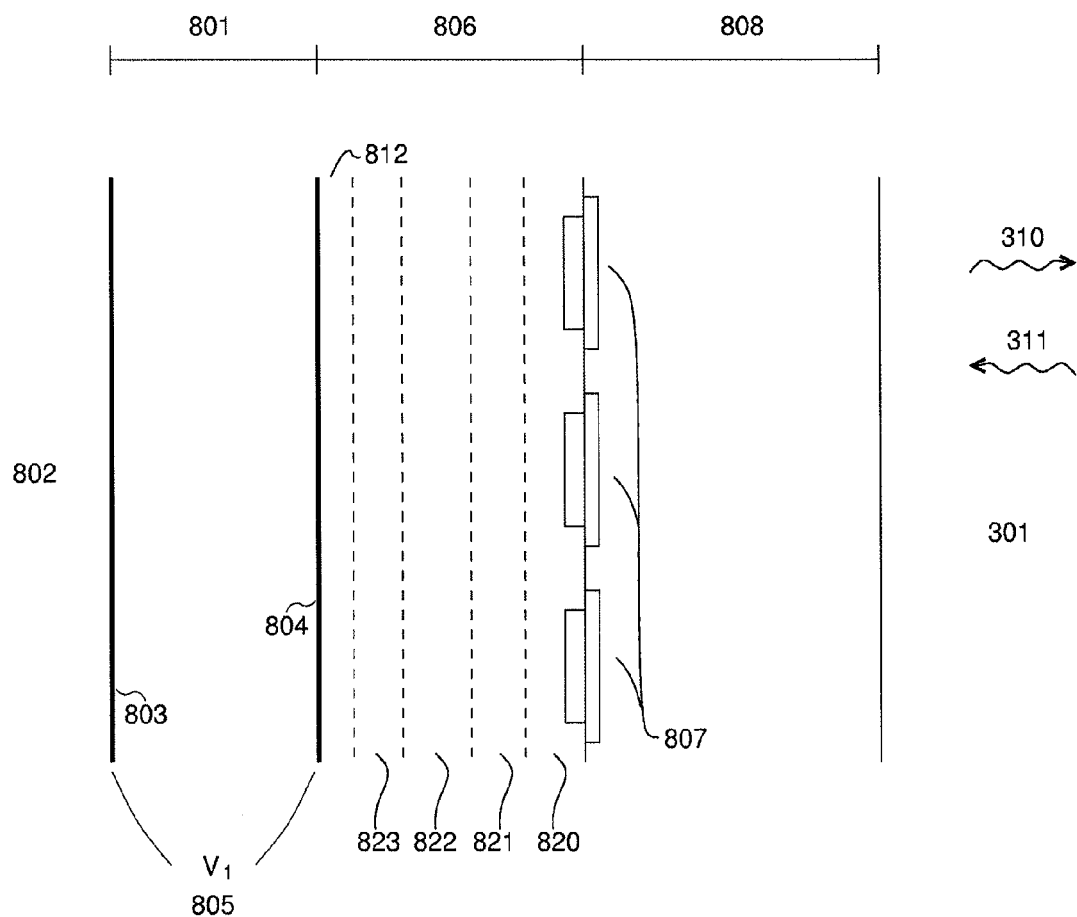

The acoustic velocity of Si is 8.4 mm/$\square$sec and for Al it is 6.4 mm μsec. Thus, further substrate layers of electronics (typically Si-substrate layers) may be added between the cmut/pmut substrate 806 and the piezoelectric layer 801 while still maintaining the thickness of the total HF section 806 to be a fraction of the LF1 wavelength in the layers. FIG. 8b illustrates this configuration. In FIG. 8b the HF section 806 is by example composed of the cmut/pmut layer 820 mounted on 3 Si layers with integrated electronics, including a receiver amplifier layer 821 that is mounted on a sub-aperture beam forming layer 822 and a transmitter amplifier layer 823, similar to the substrate layers in FIGS. 4b-e. Electrical connection between the different layers is obtained with vias or through-holes and connecting pads according to known methods in integrated circuit technology. Alternatively, known bonding techniques may be used such as, for example, between connections at the edges of the substrates, as discussed in relation to FIG. 4b-e. With a layer thickness of 0.2 mm, the total thickness of the HF section 806 is 0.8 mm, less than $\lambda_{Si}/8$ for LF1 frequencies less than 1.319 MHz.

Figure 8C:
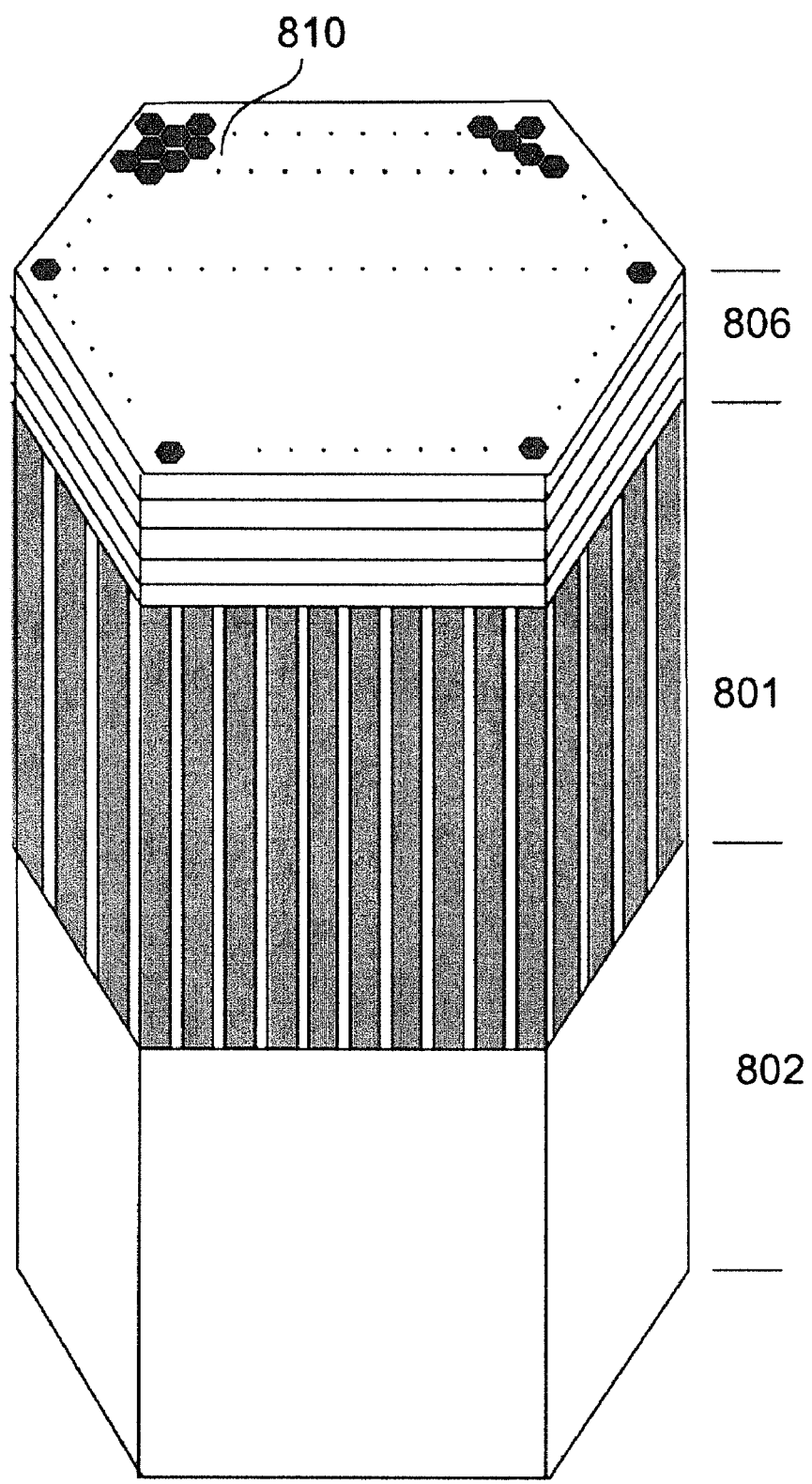

The structure is for example useful for a 2D array probe similar to the one shown in FIG. 4c. Similar apertures, number of elements, and number of sub-apertures, are used for connecting 2D array elements into linear array elements as described in relation to FIG. 4d. A perspective view of a 2D array concept probe with integrated electronics as part of the acoustic design, is illustrated in FIG. 8c. The cmut/pmut layer and the integrated circuit layers are shown as part of HF section 806 mounted on the LF1 piezoelectric layer 801 and the backing 802 with the front radiating surface 810. Connection between the instrument cable and the electronic circuits is accomplished with flex print circuitry from the back of the assembly to the edges of the circuit substrates as indicated in FIG. 4c.

The electronic layers closest to the LF1 piezo layer 801, starting with 823, can be electrically connected to the LF1 array elements, such as LF1 switches, amplifier and sub-aperture electronics. The LF1 array can also be connected to amplifier and sub-aperture electronics for example at the front of the LF1 array, at the back of the LF1 array, or inside the probe behind the backing, as discussed in relation to FIG. 4c. This can be especially advantageous when the LF1 array is used for transmit only, as described with the methods in U.S. Patent Application Publication No. 2005/0277835 and U.S. Patent Application Publication No. US 2006/0052699 A1, where only a transmit sub-aperture beam former is needed. For transmit amplifiers that switches the element signals to positive and negative power voltages, the power losses are so low that the whole transmit beam former with amplifiers can be integrated into the probe.

For cardiac applications, the aperture dimension is limited by the distance between the ribs, but for abdominal applications one could double the HF aperture diameter, which would increase the number of HF and LF1 elements by a factor of 4. In one embodiment, this increases the number of HF sub-apertures to 840, and the LF1 number of elements to 440, which also can be handled with cable connections to an instrument for beam forming. As described above, time multiplex of samples of the signals from several sub-apertures along a single wire may be used to reduce the number of wires required to connect to the instrument, where 8× time multiplex would require 105 wires to connect the HF array to the instrument.

Per the discussion above, a LF1 radiation aperture that is wider than the HF radiation aperture is often used. For parallel receive beam-forming, less than the entire HF aperture is typically used for transmit of the HF pulses to obtain a wide enough HF transmit beam. To further increase both the HF and LF1 apertures while minimizing an increase in the number of instrument channels, sparse arrays are used as discussed in relation to FIG. 11, where not all element sites are connected electrically. This technique introduces grating lobes, but designing the sparse arrays so that potential grating lobes from the LF1 and HF apertures do not overlap, the effect of grating lobes in the images can be suppressed with the imaging methods described in U.S. Patent Application Publication No. 2005/0277835 and U.S. Patent Application Publication No. US 2006/0052699 A1.

Figure 9:
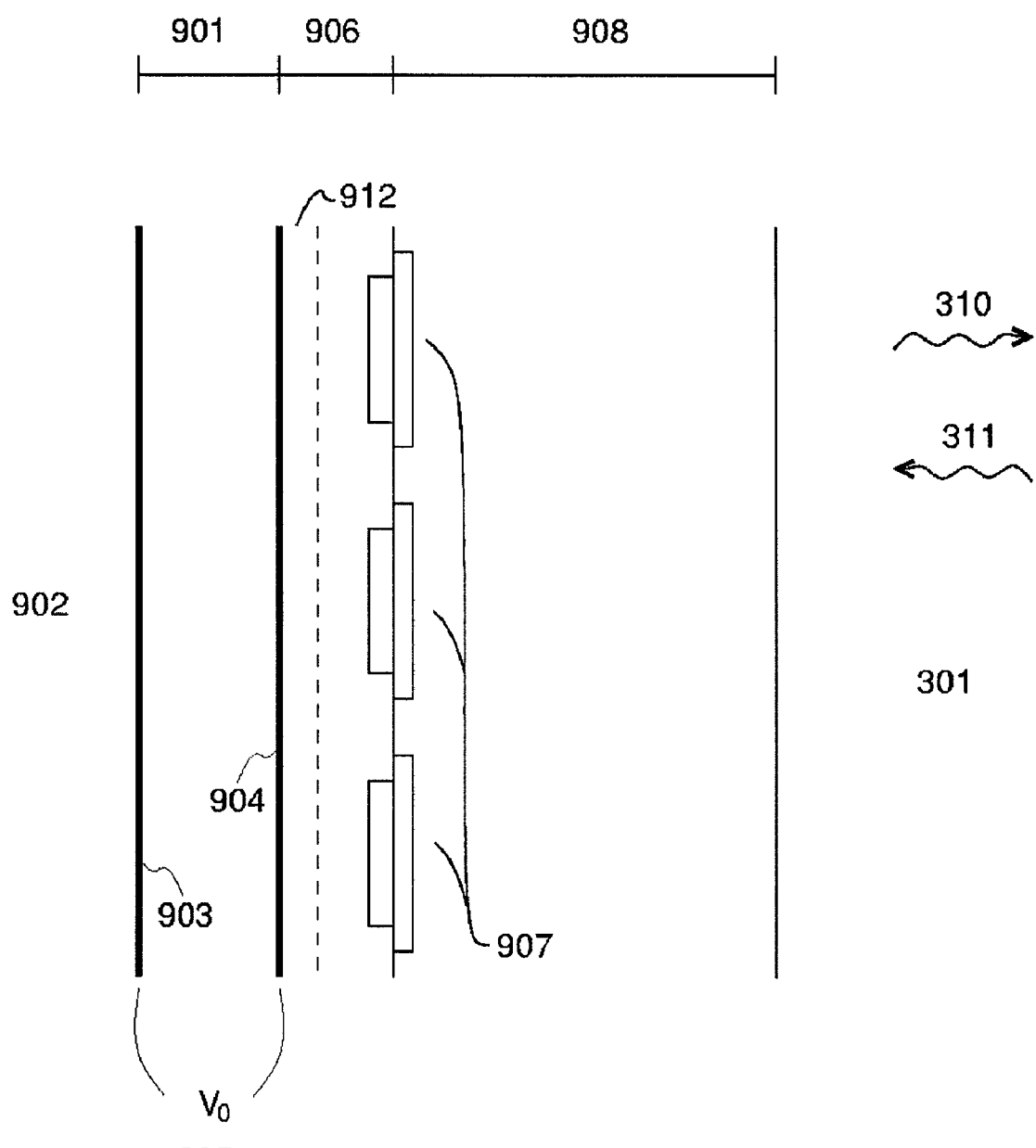
FIG. 9 shows a cross section of a transducer stack embodiment of the present invention in which LF1 transduction is generated by cmut/pmut cells on a substrate in front of a piezolayer for HF transduction.

Another example in FIG. 9 shows a cmut/pmut LF1 section 906 in front of an HF piezoelectric layer 901 made of ceramic/polymer composite mounted on a backing material 902. Element electrodes 903 and 904 constitute the HF element electric port 905. LF1 transduction is provided by cmut/pmut drums 907 arranged on the substrate layer of the LF1 section 906. Details of the cmut/pmut drums 907 with electrodes and electrical coupling are not shown and are made according to known or hereafter developed techniques. By making the piezoelectric layer 901 as a ceramic/polymer composite, the acoustic impedance of the piezoelectric layer 901 is matched to the effective acoustic impedance of the LF1 section 906 (i.e., Si layer) with drums 907 to define the HF acoustic resonance. In front of this structure, acoustic impedance matching layers (typically one or two) 908 connect the HF and LF1 sections acoustically to the load material 301 for transmitting generated waves 310 and receiving incoming waves 311 in the load material. These matching layers 908 can also be used to reduce lateral coupling between the LF1 array elements through absorption. The acoustic matching section is together with the cmut/pmut layer 906 used to increase the bandwidth of the HF electro/acoustic transfer function, and will at the low frequency function as an acoustically thin protection cover layer for the LF1 array 906, where the stiffness of the cmut/pmut membranes is tuned to the acoustic layer/load transfer. Due to the high longitudinal wave velocity of Si (8.44 mm/$\Box$sec), the thickness of the Si substrate can be made adequately thin for acceptable effect on the HF electro/acoustic transfer function. To further limit lateral coupling inside the Si substrate an optional absorbing isolation layer 912 is arranged at the back of the Si substrate, the isolation being made adequately thin at the high frequencies to have limited effect on the HF transfer function.

The layered structure in FIG. 9 has advantages for 2D arrays for three-dimensional (3D) beam steering and imaging, where electrical access to the large number (~3000) of HF elements is provided from the back of the array structure for simplest connection to cable or sub-aperture beam forming electronics. The LF1 2D array will have much fewer elements (1/50-1/100 of the HF number) simplifying the connection to the LF1 elements, for example with thin wires through the backing material 902, where also simplified connection techniques are available with the cmut/pmut manufacturing technology.

Figure 10A:
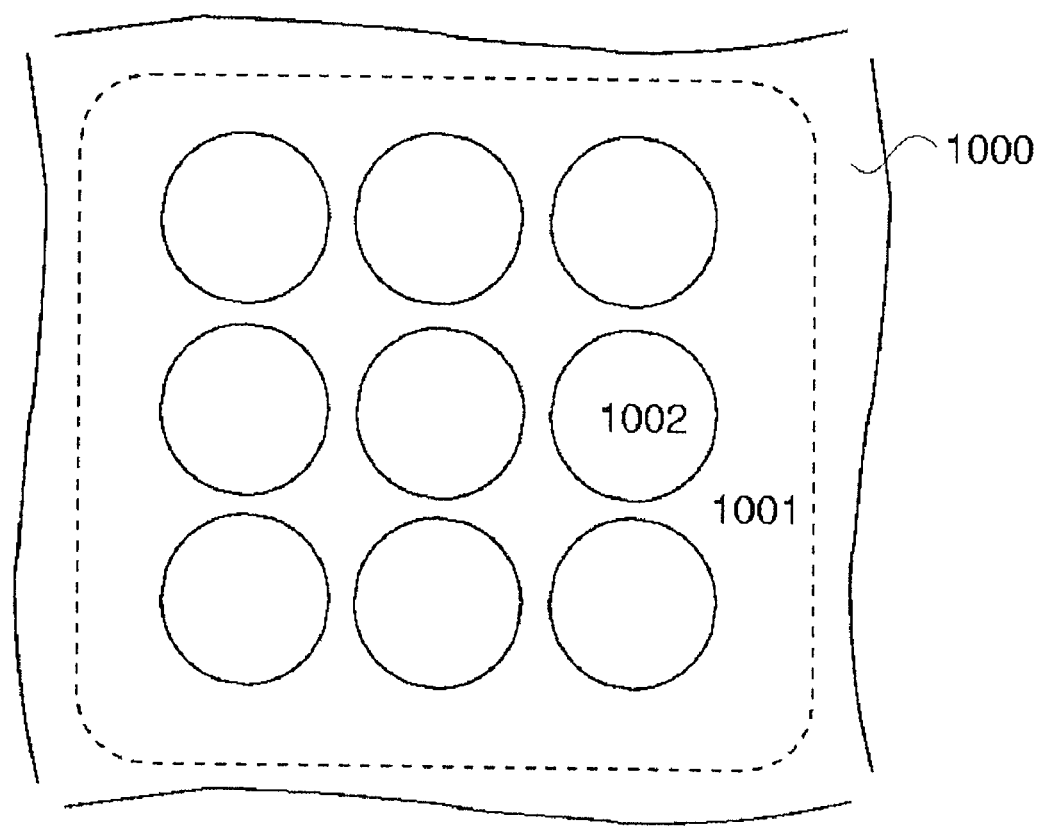
FIGS. 10a and 10b are front and cross section view of a combined LF1 and HF section implemented by cmut/pmut transduction cells micro-machined on a substrate, where the HF cells are placed on top of the LF1 cells.
Figure 10B:
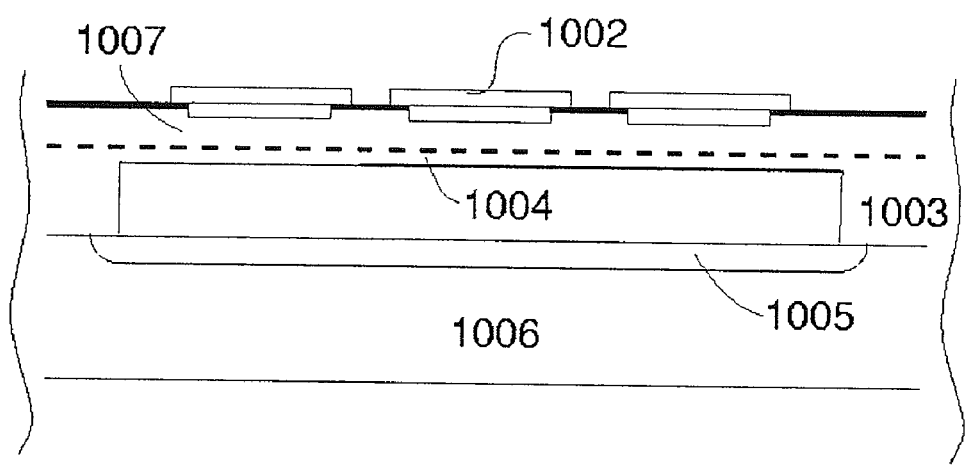

The invention further presents a solution to the LF/HF transduction with common radiation surface where high frequency cmut/pmut cells are mounted on top of low frequency cells. FIG. 10a shows a substrate front 1000 with one low frequency cell 1001, and several high frequency cells 1002 on top of the low frequency cell. As the low frequency allows large dimensions of the low frequency cell, this cell might be micro-machined from the back side of the substrate as indicated in FIG. 10b which shows a cross section through a first substrate 1003 where etching from the substrate back side provides the thin low frequency membrane 1004 in capacitive interaction with an electrode 1005 that is mounted on or part of a second substrate 1006 that is attached to the first substrate 1003 through gluing or other bonding techniques. Several high frequency cells 1002 are micromachined on the front of the low frequency membrane 1004. With more complex manufacturing techniques, both the low and the high frequency cells can be manufactured from the front side. Other cmut/pmut solutions known or hereafter developed may also be used to implement the cells. The present description describes how to transmit both the LF1 and HF pulses from the same radiation surface. However, when Si is used as a substrate, FIG. 10b indicates LF1 electrode solutions where a front layer 1007 of the Si-substrate is highly n-doped (n++) to provide a common ground electrode for the LF1 and HF cells. The hot LF1 electrode could similarly be obtained by high n-doping of a region 1005 of the second Si-substrate 1006.

Figure 11:
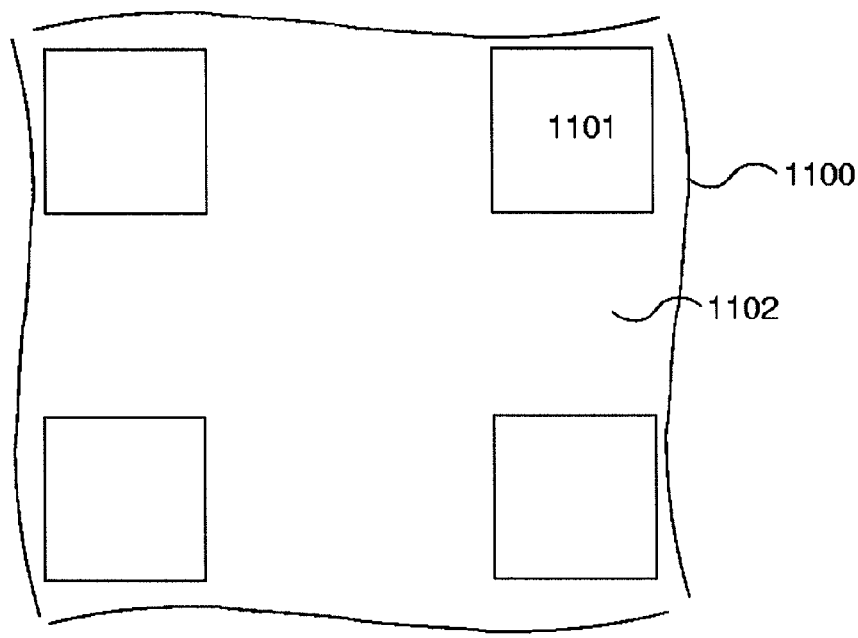
FIG. 11 is a front view of a LF1 and HF array arranged as a sparse array where the HF and LF1 elements are placed between each other.

Dual frequency band operation with widely separated frequency bands can also conveniently be implemented as sparse arrays, where the low and the high frequency elements are placed at different locations on the array surface, but sufficiently close so that outside a certain distance from the array, the two frequency beams appear to originate from at least partially the same radiating surface. 2D sparse arrays are especially useful for 3D acoustic imaging where the sparse arrays allow two-dimensional direction steering of the acoustic beam with a reduced number of elements (~1000). 2D sparse arrays are also useful for corrections for wave front aberrations and pulse reverberations, both with 2D and 3D beam scanning. FIG. 11 shown an embodiment with part of an array surface 1100 having four LF1 array elements 1101 with open space 1102 in between for placement of HF array elements in a sparse array pattern. Sparse arrays produce grating lobes in off-set directions from the beam main lobe, where the transmit and receive apertures must be designed for non-overlapping directions of the grating lobes. For imaging methods that are based on the nonlinear interaction between the dual frequency beams, for example as described in U.S. Patent Application Publication No. 2005/0277835 and U.S. Patent Application Publication No. US 2006/0052699 A1, improved suppression of the grating lobes in the image is achieved when the grating lobes for the LF1 and HF beams are non-overlapping. In fact, because of the large wavelength of the low band (λ~3 mm @ 500 kHz), it is possible to design an array with small low frequency array elements that do not have low frequency grating lobes but still with so large distance between the elements (~2 mm) that one can place many high frequency elements between the low frequency elements.

With resonant bulk piezo-ceramic elements for the electro-acoustic transduction similar to FIG. 3, sparse arrays may be used, for example, to manufacture a high frequency array with division of all its elements. A subgroup of these element locations is selected for the LF1 elements which are produced by attaching a piezo-ceramic slab at the back of said selected HF elements. Electrical connections are made between the front electrode of the high frequency element, which is commonly the ground electrode, and a back electrode of said attached piezo-ceramic slab. With less electro-acoustic transduction efficiency, the resonance frequency for the LF1 elements is reduced by attaching a mass of a heavy and stiff material, for example metals like Cu, Ag, Au, Pd, Pt, or W at the back of the selected HF elements, and use the surface electrodes of the high frequency piezo-ceramic element for transduction.

Figure 12:
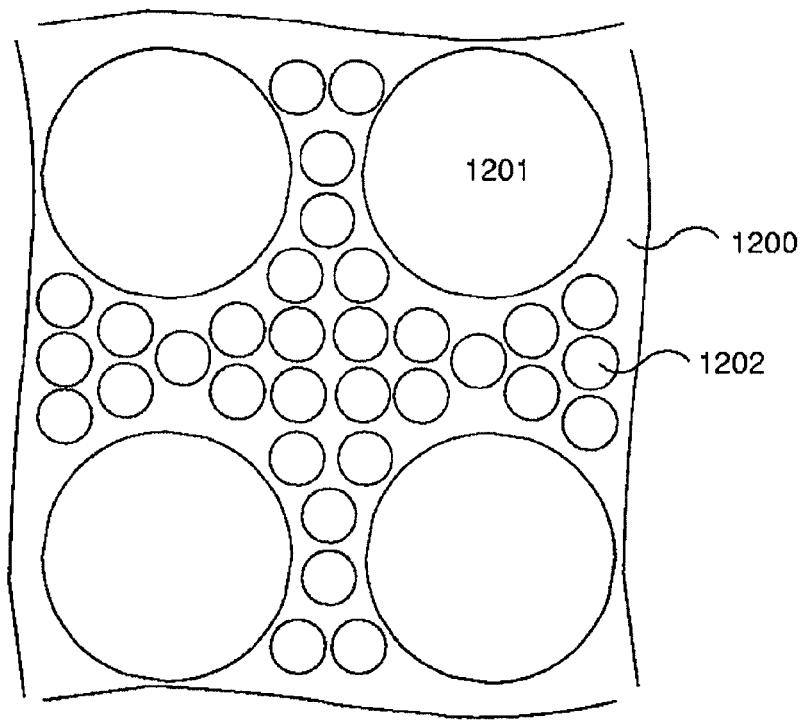
FIG. 12 is a front view of a combined low and high frequency section implemented by cmut/pmut transduction cells micro-machined on a substrate, where the low and high frequency cells are placed side by side.

Micro machined transduction elements on the front of a Si-substrate are also well suited for sparse array implementation of the dual frequency array, as the large low frequency cells and the smaller high frequency cells are machined at different locations on the array surface, as for example shown in FIG. 12. Cmut/pmut cells 1201 for the low frequency band are arranged on the substrate 1200 and are encircled by cmut/pmut cells 1202 for the high frequency band. The high frequency band cells 1202 are electrically connected to form high frequency elements, while the low frequency band cells 1201 are connected to form larger low frequency elements, for example as illustrated for the phased array in FIG. 5. Typically several cells are electrically connected for each array element.

Figure 13A:
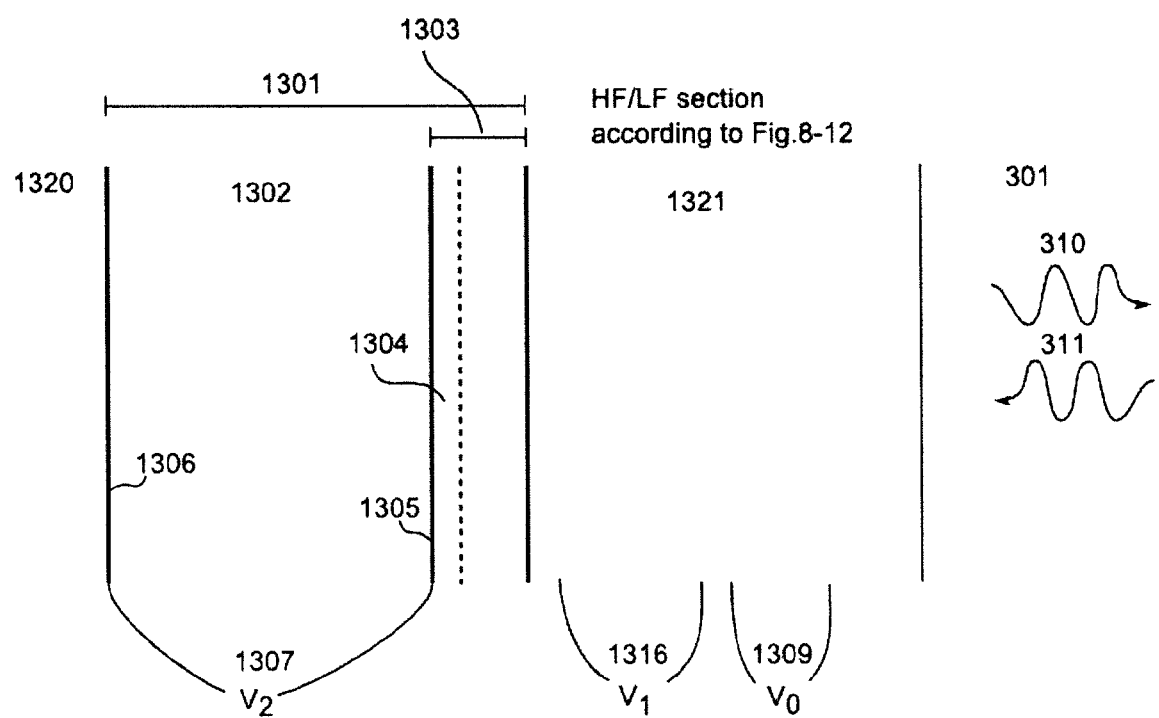
FIGS. 13a and 13b are cross section and top views of an embodiment with a third electro-acoustic transduction band obtained with the cmut/pmut structures in accordance with the embodiments of FIGS. 8a-12.

Acousto-electric transduction in a second LF2 band may also be obtained with the cmut/pmut solutions in FIGS. 8-12 for a, HF and a first LF1 band, and adding structures 1301 for the LF2 band as illustrated in FIG. 13a. The structure to represent the HF and LF1 transduction according to one of FIGS. 8-12 is indicated by 1321, with acoustic coupling to the load material 301, and with the HF electric port 1309 and LF1 electric port 1316. The LF2 electro acoustic transduction is in this embodiment according to the invention is obtained with piezoelectric layer 1302 mounted on backing material 1320 with an isolation section 1303 to the front with the same functionality as in relation to FIG. 3e. When the piezoelectric layer 1302 is made as a composite, the isolation section 1301 is conveniently made of a least two layers with for example a back layer 1305, according to the discussion above in relation to FIG. 3d. The electrodes 1305 and 1306 produce LF2 electric port 1307 which couples acoustically to the load through the HF/LF1 structure 1321.

An acoustic transducer array probe with 3 band operation is also obtained with the structure in FIG. 13a with a triple membrane cmut/pmut solution similar to FIGS. 10 and 12, where the LF1 band is operated with the piezoelectric layer at the location of 1302 and the LF2 band is operated by the large membranes 1001 in FIG. 10 or 1201 in FIG. 12. Yet another embodiment is a structure as in FIGS. 10 and 12 where one of the membranes 1001/1002 in FIG. 10 or 1201/1292 in FIG. 12 has dual resonance frequencies, so that three resonance frequencies are obtained with two membranes. Typically, the large membranes 1001 or 1201 operate both the LF1 and LF2 bands, while the smaller membranes 1002 or 1202 operate at the HF band, or the smaller membranes 1002 or 1202 operate the HF and LF1 bands, while the large membranes 1001 or 1201 operates the LF2 band.

Figure 13B:
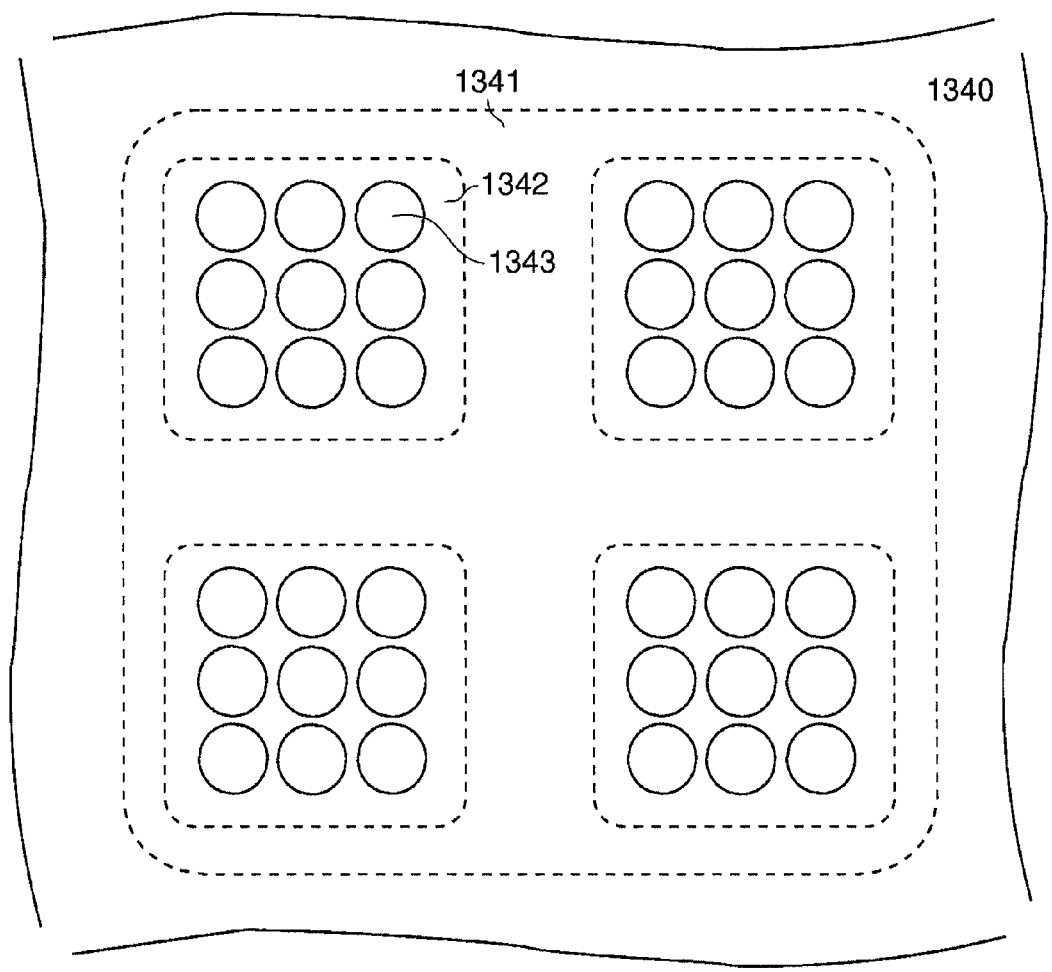

In yet another embodiment, three separate membranes are used for the LF2, the LF1, and the HF bands, for example as shown in FIG. 13b, where 1343 shows the HF membranes mounted on top of the LF1 membranes 1342 which again are mounted on top of the LF2 membranes 1341 on the common substrate 1340. Alternatively one could mount all the membranes by the side of each other similar to that in FIG. 12, or one membrane type mounted on the top of one of the other types, while the third membrane type is mounted by the side of the others.

FIGS. 13a and b show examples of embodiments that allow electro-acoustic transduction in 3 frequency bands. The radiation surfaces are typically divided into arrays of elements for steering of the focus and/or the direction of the beams at all three frequency bands. Typical arrays could be annular, linear, 1.5D, 1.57D, and 2D arrays. The lateral width of the elements (element radiation surface) is then related to the acoustic wavelength in the object 301 for the different frequency bands. The HF array would then require the lowest element width, with intermediate width elements for the LF1 array, and largest width for the LF2 array, and so on. A layer structure as in FIG. 13a, b is typically used across the whole array width, wherein array elements for each frequency band are defined with electrodes and cuts in ceramic layers. With the two layer isolation structures 317 (HF) and 1303 one is less sensitive to location of cuts between the HF, LF1, and LF2 ceramic layers (See discussion in relation to FIG. 3b-e). Typically each of the piezoelectric layers is made as piezo-ceramic/polymer composites, and the elements of these layers would then be defined by the division between the electrodes on the composite surfaces at the cuts through the ceramic layers. This allows different dimensions and even different shapes of the elements for the different frequency bands, as described above.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention.

It is also expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed:

1. An acoustic transducer array probe for transmission from a front face of said probe of acoustic waves in a high frequency (HF) band and at least a $1^{St}$ lower frequency (LF1) band and reception of acoustic waves at least in the HF band, the acoustic transducer array probe comprising:
    a transducer structure including different arrays of transducer elements configured for respective HF and the LF1 electro-acoustic transduction, the array for the HF electro-acoustic transduction having HF array elements and the array for the LF1 electro-acoustic transduction having LF1 array elements, and
    radiation surfaces for the HF band and the LF1 band, wherein at least a portion of said radiation surfaces for the HF and LF1 bands is common in a same common radiation surface region of the transducer structure, wherein the LF1 array elements within the common radiation surface have larger radiation surfaces with larger distance between neighboring element centers, than do the HF array elements within the common radiation surface, and
    wherein the radiation surfaces include at least an LF1 transmit surface for LF1 band transmission and an HF transmit surface for HF band transmission, an outer boundary of said LF1 transmit surface extends at least in a region outside an outer boundary of said HF transmit surface.

2. An acoustic transducer array probe according to claim 1, wherein said array for HF electro-acoustic transduction and said array for LF1 electro-acoustic transduction are independently arranged as one of
    a single element array, and
    an annular array of transducer elements, and
    a linear array of transducer elements, and
    a curved array of transducer elements, and
    a two dimensional array of transducer elements, and
    a composition of transducer elements of any form.

3. An acoustic transducer array probe according to claim 1, wherein
    a thickness of the transducer structure of the different arrays is constant throughout an entire radiation surface of the transducer structure including the radiation surfaces for the HF and LF1 bands, and sizes of LF1 and HF transmit and receive apertures are selectable electrically by an electrical connection to the transducer elements.

4. An acoustic transducer array probe according to claim 1, wherein the radiation surfaces also include an HF receive surface for HF band reception, and the transducer elements are selectively activable so that the HF receive surface is larger than the LF1 transmit surface.

5. An acoustic array probe according to claim 1, wherein
    said radiation surfaces include an HF transmit surface, an LF1 transmit surface, and at least one of an HF receive surface and an LF1 receive surface, wherein at least one of said radiation surfaces is made as a sparse array of said transducer elements, and wherein
    said sparse arrays are designed so that HF potential grating lobes of said sparse HF transmit array are directed relative to an LF1 beam so that an LF1 pulse pressure of an LF1 pulse at an HF pulse in said HF grating lobes is so low that nonlinear manipulation of object elasticity by the LF1 pulse at the HF pulse is negligible along said HF grating lobes compared to along an HF main lobe.

6. An acoustic transducer array probe according to claim 1, further comprising at least one electronic substrate layer with integrated electronics circuits connecting to array elements, the at least one electronic substrate layer is at least one of:
    stacked within said different physical structures of said HF and LF1 array elements, and
    mounted behind said different physical structures of said HF and LF1 array elements.

7. An acoustic transducer array probe according to claim 6, wherein said at least one electronic substrate layer with electronic circuits include one or more of
    a) receiver amplifiers connected to array elements,
    b) transmitter amplifiers connected to array elements,
    c) electronic switches that connect selectable array elements or groups of array elements to single channels that further connect to an instrument,
    d) sub-aperture circuits, wherein each sub-aperture circuit connects to a sub-aperture group of array elements, and adding delays to individual signals of the each sub-aperture circuit before summing the delayed signals to form sub-aperture signals where each of the sub-aperture signals connects to a single one of the channels that further connects to an instrument,
    e) time multiplex circuits that time multiplexes samples of signals from groups of elements or groups of sub-apertures of elements on the single channels that further connect to an instrument.

8. An acoustic transducer array probe according to claim 1, wherein a thickness of the transducer structure of the different arrays is constant throughout an entire array surface including the radiation surfaces for the HF band and the LF1 band, and wherein each of the different arrays of transducer elements comprise array element electrodes defining a size of HF and LF1 transmit and receive apertures.

9. An acoustic transducer array probe according to claim 8, where an electrical connection to the array element electrodes is electronically selectable, and a size of HF and LF1 transmit and receive apertures are selected electronically by the electrical connection to the array element electrodes.

10. An acoustic transducer array probe according to claim 1, further comprising a further array of transducer elements for electro-acoustic transduction in at least one lower frequency band LF2 through at least said common radiation surface region, the electro-acoustic transduction for said at least one lower frequency band being obtained with electro-acoustic transduction structures for each of said at least one lower frequency band, at least parts of a radiation surface of said at least one lower frequency band are common with the common radiation surface region of the HF and LF1 bands.

11. An acoustic transducer array probe according to claim 10, where the electro-acoustic transduction for each of said at least one lower frequency band is obtained with a piezoelectric layer placed behind the transduction structures for HF, LF1 and any other higher frequency bands.

12. An acoustic transducer array probe according to claim 11, where an acoustic isolation section is placed to a front of each piezoelectric layer, where said isolation section provides backwards acoustic attenuation for vibrations in the resonant band of the transduction structure to the front of said each piezoelectric layer.

13. An acoustic transducer array probe according to claim 10, where the one of the HF, LF1, and LF2 arrays for imaging is determined by one of i) automatically by an application situation and ii) manually by the operator.

14. An acoustic transducer array probe for transmission from a front face of said probe of acoustic waves in a high frequency (HF) band and at least a $1^{st}$ lower frequency (LF1) band and reception of acoustic waves in at least the HF band, the acoustic transducer array probe comprising:
   a transducer structure including different arrays of transducer elements configured for respective HF and the LF1 electro-acoustic transduction, the array for the HF electro-acoustic transduction having HF array elements and the array for the LF1 electro-acoustic transduction having LF1 array elements, and
   radiation surfaces for the HF band and the LF1 band, wherein at least a portion of said radiation surfaces for the HF and LF1 bands is common in a same common radiation surface region of the transducer structure, wherein LF1 the array elements within the common radiation surface have larger radiation surfaces with larger distance between neighboring element centers, than do the HF array elements within the common radiation surface, and
   wherein the radiation surfaces include at least an LF1 transmit surface for LF1 band transmission and an HF transmit surface for HF band transmission, said LF1 transmit surface being not common with the HF transmit surface in a region around the center of said LF1 transmit surface.

15. An acoustic transducer array probe according to claim 14, wherein said array for HF electro-acoustic transduction and said array for LF1 electro-acoustic transduction are independently arranged as one of
   a single element array, and
   an annular array of transducer elements, and
   a linear array of transducer elements, and
   a curved array of transducer elements, and
   a two dimensional array of transducer elements, and
   a composition of transducer elements of any form.

16. An acoustic transducer array probe according to claim 14, wherein
   a thickness of the transducer structure of the different arrays is constant throughout an entire radiation surface of the transducer structure including the radiation surfaces for the HF and LF1 bands, and sizes of LF1 and HF transmit and receive apertures are selectable electrically by an electrical connection to the transducer elements.

17. An acoustic transducer array probe according to claim 14, wherein the radiation surfaces also include an HF receive surface for HF band reception, and the transducer elements are selectively activable so that the HF receive surface is larger than the LF1 transmit surface.

18. An acoustic transducer array probe according to claim 14, where the HF and LF1 array elements have different shapes.

19. An acoustic transducer array probe according to claim 14, wherein the thickness of the transducer structure is the same throughout an entire array surface including the radiation surfaces for the HF band and the LF1 band, and wherein each of the different arrays of transducer elements comprise array element electrodes defining a size of HF and LF1 transmit and receive apertures.

20. An acoustic transducer array probe for transmission from a front face of said probe of acoustic waves in a high frequency (HF) band and a at least a $1^{st}$ lower frequency (LF1) band and reception of acoustic waves in at least the HF band, the acoustic transducer array probe comprising:
   a transducer structure including radiation surfaces for the HF band and the LF1 band including at least an HF transmit surface for HF band transmission and an LF1 transmit surface for LF1 band transmission, wherein at least a portion of said radiation surfaces for the HF and LF1 bands are common in a same common radiation surface region of the transducer structure, and
   the transducer structure further including HF array elements and LF1 array elements, at least said LF1 array elements being selectively activable so that a size of the LF1 transmit surface can selectively be varied to be one of
   a) a outer boundary of the LF1 surface is equal to an outer boundary of the HF transmit surface,
   b) the outer boundary of the LF1 surface is at least in a region outside the outer boundary of the HF transmit surface,
   c) there is no active LF1 transmit surface in a central region of said LF1 transmit surface, and
   d) a combination of a) and c, and
   e) a combination of b) and c)
   and wherein the LF1 array elements within the common radiation surface have larger radiation surfaces with a larger distance between neighboring element centers, than do the HF array elements within the common radiation surface.

21. An acoustic transducer array probe for transmission from a front face of said probe of acoustic waves in a high frequency (HF) band and at least a $1^{st}$ lower frequency (LF1) band and reception of acoustic waves in at least the HF band, the acoustic transducer array probe comprising:
   radiation surfaces for the HF band and the LF1 band, wherein at least a portion of said radiation surfaces for the HF and LF1 bands are common in a same common radiation surface region of the transducer structure, and
   at least in a region of the common radiation surface region, a stack of layers stacked in a thickness direction substantially normal to the common radiation surface region, said stack including separate HF and LF1 piezoelectric layers configured for respective HF and LF1 electro-acoustic transduction, wherein said HF piezoelectric layer is disposed closer to the common radiation surface region than is said LF1 piezoelectric layer, and an acoustic isolation section composed of at least two acoustic layers stacked in the thickness direction and disposed between said HF and LF1 piezoelectric layers.

22. An acoustic transducer array probe according to claim 21, wherein said isolation section includes a back layer with characteristic acoustic impedance greater than 17 MRayl and at least one layer with characteristic impedance less than 5 MRayl.

23. An acoustic transducer array probe according to claim 22, wherein said back layer is made of one of materials Cu, Ag, Au, Pd, Pt, W, or alloys of these materials, or powders of the one of the materials Cu, Ag, Au, Pd, Pt, W, or alloys of these materials, the powders being sintered or glued together.

24. An acoustic transducer array probe according to claim 21, wherein a back layer of said isolation section comprises a ceramic layer.

25. An acoustic transducer array probe according to claim 24, wherein said LF1 piezoelectric layer is made from material comprising a ceramic/polymer composite wherein the ceramic/polymer composite is diced from the back and not fully through said LF1 piezoelectric layer, so that a front portion of said ceramic piezoelectric layer forms a laterally continuous layer that forms said back layer of said isolation section.

26. An acoustic transducer array probe according to claim 25, wherein a $2^{nd}$ layer from the back of said isolation section is made of one of materials Cu, Ag, Au, Pd, Pt, W, or alloys of these materials, or powders of the one of the materials Cu, Ag, Au, Pd, Pt, W, or alloys of these materials, the powders being sintered or glued together.

27. An acoustic array probe according to claim 21, wherein said radiation surfaces include an HF transmit surface, an LF1 transmit surface, and at least one of an HF receive surface and an LF1 receive surface, wherein at least one of said radiation surfaces is made as a sparse array of said transducer elements, and where said sparse arrays are designed so that potential HF grating lobes of said sparse HF transmit array are directed relative to an LF1 beam so that an LF1 pulse pressure of an LF1 pulse at an HF pulse in said HF grating lobes is so low that the nonlinear manipulation of the object elasticity by the LF1 pulse at the HF pulse is negligible along said HF grating lobes compared to along the HF main lobe.

28. An acoustic transducer array probe according to claim 21, wherein the radiation surfaces also include an HF receive surface for HF band reception, and the transducer elements are selectively activatable so that the HF receive surface is larger than the LF1 transmit surface.

29. An acoustic transducer array probe according to claim 21, wherein a thickness of the stack is constant throughout the entire common radiation surface region, and sizes of HF and LF1 transmit and receive apertures are selectable electrically by an electrical connection to array elements in the stack.

30. An acoustic transducer array probe according to claim 21, where at least one electronic substrate layer with integrated electronics circuits connecting to array elements is stacked in the stack of layers and being one of:
  part of said acoustic isolation section, and
  mounted to a back of said HF piezoelectric layer, and
  mounted to a front of said HF piezoelectric layer, and
  mounted to a back of said LF1 piezoelectric layer, and
  electronic substrate layers are mounted to the back of a backing material.

31. An acoustic transducer array probe according to claim 30, wherein said at least one electronic substrate layer with electronic circuits include one or more of
  a) receiver pre-amplifiers connected to array elements,
  b) transmitter amplifiers connected to array elements,
  c) electronic switches that connect selectable array elements or groups of array elements to single channels that further connect to an instrument,
  d) sub-aperture circuits, wherein each sub-aperture circuit connects to a sub-aperture group of array elements, and adding delays to individual signals of the each sub-aperture circuit before summing the delayed signals to form sub-aperture signals where each of the sub-aperture signals connects to a single one of the channels that further connects to an instrument,
  e) time multiplex circuits that time multiplexes samples of signals from groups of elements or groups of sub-apertures of elements on the single channels that further connect to an instrument.

32. An acoustic transducer array probe according to claim 21, wherein acoustic waves in at least one further lower frequency band (LF2) can be transmitted and received through at least said common radiation surface,
  the electro-acoustic transduction for each of said at least one further lower frequency band is obtained with an additional electro-acoustic transduction structure composed of a piezoelectric layer with an acoustic isolation section to the front,
  said isolation section is placed in acoustic contact with a back-side of a transduction section for a next higher frequency band, and wherein
  said isolation section provides backwards isolation of vibrations in the next higher frequency band of a neighbor transduction section to the front.

33. An acoustic transducer array probe for transmission from a front face of said probe of acoustic waves in a high frequency (HF) band and a at least a $1^{st}$ lower frequency (LF1) band and reception of acoustic waves in at least the HF band, the acoustic transducer array probe comprising:
  radiation surfaces for the HF band and the LF1 band, wherein at least a portion of said radiation surfaces for the HF and LF1 bands are common in a same common radiation surface region of the front face, and
  at least in a region of the common radiation surface region, a stack of layers stacked in a thickness direction substantially normal to the common radiation surface region, wherein said stack includes a piezoelectric layer configured for one of HF electro acoustic transduction and LF1 electro acoustic transduction, and a substrate layer with cmut/pmut based transduction membranes on a front face configured for the other of HF electro acoustic transduction and LF1 electro acoustic transduction, wherein
  the stack of layers includes HF array elements and LF1 array elements respectively in the region of the radiation surfaces for the HF band and the LF1 band, the LF1 array elements within the common radiation surface region having larger radiation surfaces with larger distance between neighboring element centers, than do the HF array elements within the common radiation surface region, and wherein
  said substrate layer based on cmut/pmut transduction membranes is placed to the front of said piezoelectric layer.

34. An acoustic transducer array probe according to claim 33, wherein said LF1 electro acoustic transduction is obtained by said piezoelectric layer.

35. An acoustic transducer array probe according to claim 33, wherein said HF electro acoustic transduction is obtained by said piezoelectric layer.

36. An acoustic array probe according to claim 33, wherein said radiation surfaces include an HF transmit surface, an LF1 transmit surface, and at least one of an HF receive surface and an LF1 receive surface, wherein at least one of said radiation surfaces is made as a sparse array of said transducer elements, and where said sparse arrays are designed so that potential HF grating lobes of said sparse HF transmit array are directed relative to an LF1 beam so that an LF1 pulse pressure of an LF1 pulse at an HF pulse in said HF grating lobes is so low that nonlinear manipulation of object elasticity by the LF1 pulse at the HF pulse is negligible along said HF grating lobes compared to along an HF main lobe.

37. An acoustic transducer array probe according to claim 33, wherein the radiation surfaces also include an HF receive surface for HF band reception, and the transducer elements are selectively activatable so that the HF receive surface is larger than the LF1 transmit surface.

38. An acoustic transducer array probe according to claim 33, wherein at least one electronic substrate layer with integrated electronics circuits connecting to array elements is arranged at least at one of:
  a back of said substrate layer with cmut/pmut membranes,
  a back of said piezoelectric layer, and
  a back of a backing material.

39. An acoustic transducer array probe according to claim 38, wherein said at least one electronic substrate layer with electronic circuits include one or more of
  a) receiver pre-amplifiers connected to array elements,
  b) transmitter amplifiers connected to array elements,
  c) electronic switches that connect selectable array elements or groups of array elements to single channels that further connect to an instrument,
  d) sub-aperture circuits, wherein each sub-aperture circuit connects to a sub-aperture group of array elements, and adding delays to individual signals of the each sub-aperture circuit before summing the delayed signals to form sub-aperture signals where each of the sub-aperture signals connects to a single one of the channels that further connects to an instrument.

40. An acoustic transducer array probe according to claim 33, wherein acoustic waves in at least one further lower frequency bands band (LF2) can be transmitted and received through at least said common radiation surface,
  the electro-acoustic transduction for each of said at least one further lower frequency band is obtained with an additional electro-acoustic transduction structure composed of a piezoelectric layer with an acoustic isolation section to the front,
  said isolation section is placed in acoustic contact with a back-side of a transduction section for a next higher frequency band, and
  said isolation section provides backwards isolation of vibrations in the next higher frequency band of a neighbor transduction section to the front.

41. An acoustic transducer array probe for transmission from a front face of said probe of acoustic waves in a high frequency (HF) band and at least a $1^{st}$ lower frequency (LF1) band and reception of acoustic waves in at least the HF band, the acoustic transducer array probe comprising:
  radiation surfaces for the HF band and the LF1 band, wherein at least a portion of said radiation surfaces for the HF and LF1 bands are common in a same common radiation surface region, and
  a substrate wherein at least in a region of the common radiation surface region, separate cmut/pmut based HF and LF1 transduction membranes are arranged on said substrate and configured for respective HF and LF1 electro acoustic transductions, and wherein
  said HF and LF1 transduction membranes form HF array elements and LF1 array elements within the common radiation surface region, the LF1 array elements within the common radiation surface region having larger radiation surfaces with larger distance between neighboring element centers, than do the HF array elements within the common radiation surface region.

42. An acoustic transducer array probe according to claim 41, wherein within said common radiation surface region the HF transduction membranes are placed in front of the LF1 transduction membranes.

43. An acoustic transducer array probe according to claim 41, wherein within said common radiation surface region the HF transduction membranes are placed side by side of the LF1 transduction membranes, at a distance from each other such that HF and LF1 beams appear to originate from overlapping elements.

44. An acoustic array probe according to claim 41, wherein said radiation surfaces include an HF transmit surface, an LF1 transmit surface, and at least one of an HF receive surface and an LF1 receive surface, wherein at least one of said radiation surfaces is made as a sparse array of said transducer elements, and where said sparse arrays are designed so that potential HF grating lobes of said sparse HF transmit array are directed relative to an LF beam so that an LF pulse pressure of an LF pulse at an HF pulse in said HF grating lobes is so low that nonlinear manipulation of the object elasticity by the LF pulse at the HF pulse is negligible along said HF grating lobes compared to along a HF main lobe.

45. An acoustic transducer array probe according to claim 41, wherein the radiation surfaces also include an HF receive surface for HF band reception, and the transducer elements are selectively activatable so that the HF receive surface is larger than the LF1 transmit surface.

46. An acoustic transducer array probe according to claim 41, wherein at least one electronic substrate layer with integrated electronics connecting to array elements is disposed in back of said substrate layer with cmut/pmut membranes.

47. An acoustic transducer array probe according to claim 46, wherein said at least one electronic substrate layer with electronic circuits include one or more of
  a) receiver pre-amplifiers connected to array elements,
  b) transmitter amplifiers connected to array elements,
  c) electronic switches that connect selectable array elements or groups of array elements to single channels that further connect to an instrument,
  d) sub-aperture circuits, wherein each sub-aperture circuit connects to a sub-aperture group of array elements, and adding delays to individual signals of the each sub-aperture circuit before summing the delayed signals to form sub-aperture signals where each of the sub-aperture signals connects to a single one of the channels that further connects to an instrument,
  e) time multiplex circuits that time multiplexes samples of signals from groups of elements or groups of sub-apertures of elements on single channels that further connect to the instrument.

48. An acoustic transducer array probe according to claim 41, wherein additional acoustic pulses in a $2^{nd}$ lower frequency (LF2) band can be transmitted and received through the common radiation surface, the LF1 cmut/pmut membranes also having resonances in the LF2 band.

49. An acoustic transducer array probe according to claim 41, wherein additional acoustic pulses in a $2^{nd}$ lower frequency (LF2) band can be transmitted and received through the common radiation surface region, the electro-acoustic transduction for said LF2 band being obtained with cmut/ pmut LF2 membranes on the same substrate as said HF and LF1 transduction membranes, wherein one of:
- the HF and LF1 transduction membranes are placed on top of the LF2 membranes, and
- the LF2 membranes are placed by the side of the HF and LF1 transduction membranes.

50. An acoustic transducer array probe according to claim 41, wherein additional acoustic pulses in a $2^{nd}$ lower frequency (LF2) band can be transmitted and received through the common radiation surface, an electro-acoustic transduction for said LF2 band is obtained with a LF2 piezoelectric layer placed behind said HF/LF1 common substrate, such that at least part of a LF2 radiation surface is common in the common radiation surface region of said HF and LF2 array.

51. An acoustic transducer array probe according to claim 50, wherein acoustic waves in at least one further lower frequency band (LF3) can be transmitted and received through at least said common radiation surface region,
- the electro-acoustic transduction for each of said at least one further lower frequency band is obtained with an added electro-acoustic transduction structure composed of a piezoelectric layer with an acoustic isolation section to the front,
- said isolation section disposed in acoustic contact with a back-side of the transduction section for the next higher frequency band, and where
- said isolation section providing backwards isolation of vibrations in a next higher frequency band of a neighbor transduction section to the front.

* * * * *